(12) United States Patent
Albaek et al.

(10) Patent No.: US 11,267,843 B2
(45) Date of Patent: Mar. 8, 2022

(54) STEREODEFINING L-MONOMERS

(71) Applicant: Roche Innovation Center Copenhagen A/S

(72) Inventors: Nanna Albaek, Hørsholm (DK); Jacob Ravn, Hørsholm (DK); Erik Daa Funder, Hørsholm (DK)

(73) Assignee: Roche Innovation Center Copenhagen A/S, Horsholm (DK)

( * ) Notice: Subject to any disclaimer, the term of this patent is extended or adjusted under 35 U.S.C. 154(b) by 393 days.

(21) Appl. No.: 16/086,252

(22) PCT Filed: Mar. 2, 2017

(86) PCT No.: PCT/EP2017/054841
§ 371 (c)(1),
(2) Date: Sep. 18, 2018

(87) PCT Pub. No.: WO2017/157672
PCT Pub. Date: Sep. 21, 2017

(65) Prior Publication Data
US 2020/0291056 A1    Sep. 17, 2020

(30) Foreign Application Priority Data
Mar. 18, 2016 (EP) ..................... 16161089

(51) Int. Cl.
*C07H 19/16*    (2006.01)

(52) U.S. Cl.
CPC .................. *C07H 19/16* (2013.01)

(58) Field of Classification Search
CPC ................ C07H 19/06; C07H 19/16
See application file for complete search history.

(56) References Cited

U.S. PATENT DOCUMENTS

| | | | |
|---|---|---|---|
| 9,598,458 B2 * | 3/2017 | Shimizu | C07H 21/04 |
| 9,982,257 B2 * | 5/2018 | Butler | C12Q 1/6876 |
| 10,167,309 B2 * | 1/2019 | Shimizu | C07H 21/04 |
| 10,590,413 B2 * | 3/2020 | Butler | A61P 43/00 |

FOREIGN PATENT DOCUMENTS

| | | |
|---|---|---|
| JP | 2005-089441 | 4/2005 |
| JP | 2015-523316 | 8/2015 |
| JP | 2015-528002 | 9/2015 |
| WO | WO 2007/090071 | 8/2007 |
| WO | WO 2007/112754 | 10/2007 |
| WO | WO 2009/043353 | 4/2009 |
| WO | WO 2009/124238 | 10/2009 |
| WO | WO 2010/036698 | 4/2010 |
| WO | WO 2014/010250 | 1/2014 |
| WO | WO 2014/012081 | 1/2014 |
| WO | WO 2017/157672 | 9/2017 |

OTHER PUBLICATIONS

Bergstrom, "Unnatural nucleosides with unusual base pairing properties," Current Protocols in Nucleic Acid Chemistry, Jun. 1, 2009, 37(1):1.4.1-1.4.32.

Hirao et al., "Natural versus artificial creation of base pairs in DNA: origin of nucleobases from the perspectives of unnatural base pair studies," Accounts of Chemical Research, Dec. 18, 2012, 45(12):2055-2065.

International Search Report and Written Opinion in International Application No. PCT/EP2017/054841, dated May 26, 2017, 11 pages.

Iwamoto et al., "Stereocontrolled Synthesis of Oligodeoxyribonucleoside Boranophosphates by an oxazaphospholidine approach using acid-labile-protecting groups,"Tetrahedron Letters, Jun. 6, 2012, 53(33):4361-4364.

Oka et al., "Solid-phase synthesis of stereoregular oligodeoxyribonucleoside phosphorothioates using bicyclic oxazaphospholidine derivatives as monomer units.", Journal of the American Chemistiy Society, Nov. 26, 2008, 130(47):16031-16037.

Seth at al., "Synthesis and biophysical evaluation of 2',4'-constrained 2'O-methoxyethyl and 2',4'-constrained 2'O-ethyl nucleic acid analogues," Journal of Organic Chemistry, Mar. 5, 2010, 75(5):1569-1581.

Nukaga et al., Stereocontrolled Solid-Phase Synthesis of Phosphorothioate Oligoribonucleotides Using 2'- O-(2-Cyanoethoxymethyl)-nucleoside 3'- O- Oxazaphospholidine Monomers:, The Journal of Organic Chemistry, Sep. 21, 2012, 77(18):7913-7922.

Japan Office Action in Japanese Application No. 2018-548857, dated Nov. 25, 2020, 16 pages.

Wan et al., "Synthesis, biophysical properties and biological activity of second generation antisense oligonucleotides containing chiral phosphorothioate linkages," Nucleic Acids Research, 2014, 42(22):13456-13468.

* cited by examiner

*Primary Examiner* — Lawrence E Crane
(74) *Attorney, Agent, or Firm* — Smith Gambrell & Russell LLP

(57) ABSTRACT

Stereodefined phosphorothioate oligonucleotides, related nucleoside monomers and methods of synthesis of both are described. The disclosed isobutyryl protected L-LNA-G monomers have following Formula 50 or 51 where $R^3$ is independently $CH_2ODMTr$ or $CH_2OMMTr$ and $R^8$, when present, is cyanoethyl. The monomers have improved solubility and stability characteristics, resulting in improved efficacy in oligonucleotide synthesis.

4 Claims, 3 Drawing Sheets

Figure 2

Solubility 0 h

Figure 1A:
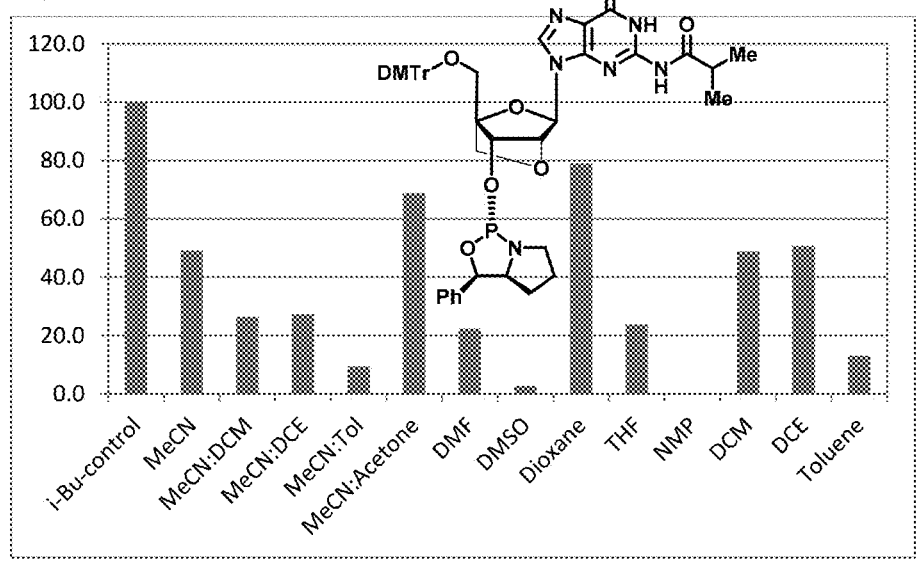

| | MeCN | MeCN:DCM (1:1) | MeCN:DCE (1:1) | MeCN:Tol. (1:1) | MeCN:Acetone (1:1) | DMF | DMSO | Dioxane | THF | NMP | DCM | DCE | Toluene |
|---|---|---|---|---|---|---|---|---|---|---|---|---|---|
| D-LNA G-DMF | yes | yes | yes | yes | yes | yes | yes | yes | yes | yes | yes | yes | yes |
| L-LNA G-DMF | no | yes | no | no | no | yes | yes | no | no | yes | yes | no | no |
| L-LNA G-iBu | yes | yes | yes | yes | yes | yes | yes | yes | yes | n/a | yes | yes | yes |

Solubility 24 h

| | MeCN | MeCN:DCM (1:1) | MeCN:DCE (1:1) | MeCN:Tol. (1:1) | MeCN:Acetone (1:1) | DMF | DMSO | Dioxane | THF | NMP | DCM | DCE | Toluene |
|---|---|---|---|---|---|---|---|---|---|---|---|---|---|
| D-LNA G-DMF | yes | yes | yes | yes | yes | yes | yes | yes | yes | yes | yes | yes | yes |
| L-LNA G-DMF | no | yes | yes | no | no | yes | yes | no | no | yes | yes | yes | no |
| L-LNA G-iBu | no | no | no | no | yes | yes | no | yes | yes | n/a | yes | yes | yes |

STEREODEFINING L-MONOMERS

CLAIM OF PRIORITY

This application is a national stage application under 35 U.S.C. § 371 of PCT Application No. PCT/EP2017/054841 filed Mar. 2, 2017, which claims priority to European Patent Application No. EP16161089.4 filed Mar. 18, 2016, of which each of these applications are hereby incorporated by reference in their entirety.

FIELD OF THE INVENTION

The present invention relates to the field of stereodefined phosphorothioate oligonucleotides and to nucleoside monomers and methods of synthesis thereof. Herein are disclosed acyl protected L-LNA-G monomers which have improved solubility and stability characteristics, and thus results in improved efficiency in oligonucleotide synthesis.

BACKGROUND TO THE INVENTION

Recently, we have discovered that the use of stereodefined phosphorothioate internucleoside linkages in LNA oligonucleotides allow for the optimisation of the pharmacological profile of LNA oligonucleotides. The manufacture of stereodefined phosphorothioate oligonucleotides is at present comparatively inefficient as compared to non stereodefined phosphorothioate oligonucleotides. There is therefore a need to improve the efficiency of synthesis of stereodefined oligonucleotides.

WO2014/010250 discloses nucleoside monomers which when incorporated into an oligonucleotide provide a chirally defined stereocenter at the corresponding phosphorothioate internucleoside linkage position. Whilst LNA monomers are considered, none have been made or tested. The present invention is based upon the surprising observation that guanine monomers (referred to as L-XNA-G monomers) are insoluble and/or unstable in many solvents. The present invention is based upon the provision of L-XNA-G monomers where the exocyclic nitrogen of the guanine residue is protected with an acyl protection group rather than the standard DMF protecting group. Such monomers are remarkable soluble and stable in solution.

STATEMENT OF INVENTION

The invention provides for a compound of formula 1, 1a or 1b

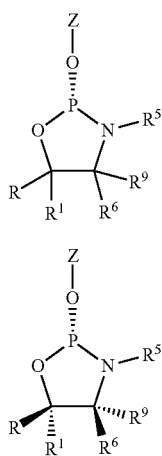

Formula 1

Formula 1a

Formula 1b wherein
Z is a guanine nucleoside wherein the guanine nucleobase group comprises an acyl protecting group on the guanine exocyclic nitrogen group, wherein the exocyclic oxygen of Formula I is covalently attached to the 3' carbon of the nucleoside Z;

$R^5$ and $R^6$ are independently selected from the group consisting of hydrogen, alkyl, cyclo-alkyl, aryl, heteroaryl, substituted alkyl, substituted cyclo-alkyl, substituted aryl, and substituted heteroaryl, or $R^5$ and $R^6$ together form a heterocyclic ring comprising 3-16 carbon atoms, together with the N atom of formula 1;

$R^9$ is hydrogen;

$R^1$ is selected from the groups consisting of hydrogen and $C_{1-3}$ alkyl; and, R is selected from the groups consisting of aryl, heteroaryl, substituted aryl, substituted heteroaryl, nitro, halogen, cyano, silyl, substituted silyl, sulfone, substituted sulfone (aryl substituted sulfone), fluorene, and substituted fluorene.

when substituted, R may be substituted with a group selected from the group consisting of: $C_{1-4}$ alkyl group, $C_{6-14}$ aryl group $C_{1-4}$, alkoxy group, $C_{7-14}$ aralkyl group, $C_{1-4}$ alkyl, $C_{6-14}$ aryl group, $C_{1-4}$ alkoxy, $C_{6-14}$ aryl group, or $C_{6-14}$ aryl $C_{1-4}$ alkyl group. Multiple substitutions may be dependently or independently selected from the group consisting of: $C_{1-4}$ alkyl group, $C_{6-14}$ aryl group $C_{1-4}$, alkoxy group, $C_{7-14}$ aralkyl group, $C_{1-4}$ alkyl, $C_{6-14}$ aryl group, $C_{1-4}$ alkoxy, $C_{6-14}$ aryl group, or $C_{6-14}$ aryl $C_{1-4}$ alkyl group.

The compound of formula 1 may be in either of the alternative diastereoisomers, as shown in formula 1a and formula 1b, or in some embodiments may be a mixture of the diastereoisomers.

In some embodiments Z is

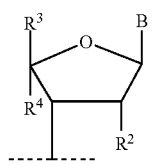

wherein B is a guanine nucleobase group comprising an acyl protecting group on the guanine exocyclic nitrogen group, and $R^2$, $R^3$ and $R^4$ are as described herein. In some embodiments $R^4$ and $R^2$ form a biradicle bridge to form a bicyclic nucleoside (see under LNA herein). The dotted line represents the linkage to the non cyclic oxygen in the compound of formula 1, 1a or 1b. Representative nucleosides groups Z are illustrated in the nucleosides of formulas 62, 63, 64, 65, 66, 67, 68, 69, 70, 71, 72, 73 & 74 as disclosed herein, with the exception that the 3'OH group is replaced with the bond to the exocyclic oxygen group shown in formulas 1, 1a and 1b.

In some embodiments, when R is substituted aryl, R may be substituted with halide, such as iodide, fluoride, bromide or chloride.

The invention provides for a solution (composition) comprising the compound of formula 1 and a solvent. The invention provides for a solution (composition) comprising the compound of formula 1a and a solvent. The invention provides for a solution (composition) comprising the compound of formula 1b and a solvent. The solution may be a stable solution, i.e. it is stable for at least 24 hours at room temperature (e.g. using the assay provided in example 6). It should be recognised that in some embodiments, a stable solution may result in some degradation of the compound of the invention in the solution during the 24 hours, but, for example at least 20% (such as at least 30%, at least 40%, at least 50%, at least 60% or at least 70%, or at least 75%) of the initial amount of compound 1 is present in the solution after 24 hours.

The invention provides for the use of the compound or the composition of the invention in the synthesis or manufacture of an oligonucleotide.

The invention provides for a method for the synthesis of a compound according to formula I (1a), said method comprising the step of reacting a guanine nucleoside comprising a 3' —OH group; with a compound of formula 8:

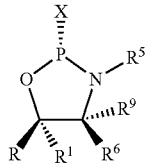

Formula 8

Wherein X is halide, such as iodide, bromide or chloride, and wherein the guanine nucleobase group on the guanine nucleoside comprises an acyl protecting group on the guanine exocyclic nitrogen group, and wherein R, $R^1$, $R^9$, $R^5$ and $R^6$ are as per the compound of the invention, and wherein the guanine nucleobase group on the guanine nucleoside comprises an acyl protecting group on the guanine exocyclic nitrogen group.

The invention provides mixtures of compounds of formula 1a and 1b. The invention provides a composition which comprises the compound of formula 1a. In some embodiments the mixtures may be a diastereomeric mixture. As is shown herein, the solubility of L and D stereoisoforms of the monomers disclosed herein, such as the LNA monomers, can exhibit remarkably different solubilities and stabilities in different solvents.

The invention provides for a method for the synthesis of a stereodefined phosphorothioate oligonucleotide, said method comprising the step of coupling the compound of the invention (the guanine nucleoside monomer of the invention) to the 5'-OH group of a nucleoside to a —OH group attached to a solid support, followed by a sulfurization step. The method may further comprise a capping step which may be performed prior to or subsequent to the sulfurization step. The acyl protection group may be subsequently removed after chain elongation is completed, for example during global deprotection and cleavage of the oligonucleotide from the solid support. The monomer of the invention may therefore be used in phosphoramidite oligonucleotide synthesis to introduce a stereodefined chiral center within the oligonucleotide.

FIGURES

Figure 1B:
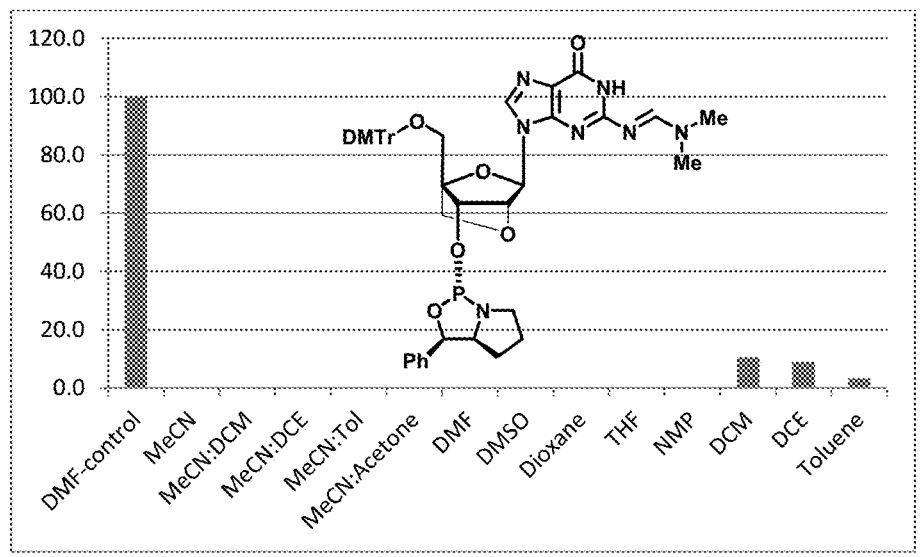

FIG. 1: Stability of L-LNA-G-iBu monomer (3a) and L-LNA-G-DMF monomer as measured after 24 hours in various solvents (see example 6). FIG. 1a—I-bu-control refers to the starting material (L-LNA G-I-bu) at t=0 h. FIG. 1b—DMF-control refers to the starting material (L-LNA G-DMF) at t=0 h.

DETAILED DESCRIPTION

As used herein, the term "aryl" refers to an aromatic ring wherein each of the atoms forming the ring is a carbon atom. Aryl rings are formed by five, six, seven, eight, nine, or more than nine carbon atoms. Aryl groups are a substituted or unsubstituted. In one aspect, an aryl is a phenyl or a naphthalenyl. Depending on the structure, an aryl group can be a monoradical or a diradical (i.e., an arylene group). In one aspect, an aryl is a $C_{6-10}$ aryl. In some embodiments aryl is phenyl. When substituted aryl may be substituted with a group selected from the group consisting of: $C_{1-4}$ alkyl group, $C_{6-14}$ aryl group $C_{1-4}$, alkoxy group, $C_{7-14}$ aralkyl group, $C_{1-4}$ alkyl, $C_{6-14}$ aryl group, $C_{1-4}$ alkoxy, $C_{6-14}$ aryl group, or $C_{6-14}$ aryl $C_{1-4}$ alkyl group. Multiple substitutions may be dependently or independently selected from the group consisting of: $C_{1-4}$ alkyl group, $C_{6-14}$ aryl group $C_{1-4}$, alkoxy group, $C_{7-14}$ aralkyl group, $C_{1-4}$ alkyl, $C_{6-14}$ aryl group, $C_{1-4}$ alkoxy, $C_{6-14}$ aryl group, or $C_{6-14}$ aryl $C_{1-4}$ alkyl group; or a group selected from the group consisting of halide, such as iodide, fluoride, bromide or chloride, such as phenyl substituted with halide, such as iodide, fluoride, bromide or chloride.

An "alkyl" group refers to an aliphatic hydrocarbon group. The alkyl moiety may be a saturated alkyl group (which means that it does not contain any units of unsaturation, e.g. carbon-carbon double bonds or carbon-carbon triple bonds) or the alkyl moiety may be an unsaturated alkyl group (which means that it contains at least one unit of unsaturation). The alkyl moiety, whether saturated or unsaturated, may be branched, straight chain, or include a cyclic portion. The point of attachment of an alkyl is at a carbon atom that is not part of a ring. The "alkyl" moiety may have 1 to 10 carbon atoms (whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms, although the present definition also covers the occurrence of the term "alkyl" where no numerical range is designated). Alkyl includes both branched and straight chain alkyl groups. The alkyl group of the compounds described herein may be designated as "$C_{1-6}$ alkyl" or similar designations. By way of example only, "$C_{1-6}$ alkyl" indicates that there are one, two, three, four, five, or six carbon atoms in the alkyl chain, i.e., the alkyl chain is selected from the group consisting of methyl, ethyl, propyl, iso-propyl, n-butyl, isobutyl, sec-butyl, and tert-butyl. Typical alkyl groups include, but are in no way limited to, methyl, ethyl, propyl, isopropyl, butyl, isobutyl, tertiary butyl, pentyl, hexyl, allyl, cyclopropylmethyl, cyclobutylmethyl, cyclopentylmethyl, cyclohexylmethyl, and the like. In one aspect, an alkyl is a $C_{1-6}$ or $C_{1-4}$ alkyl or $C_{1-3}$ alkyl. $C_{1-3}$ alkyl group means straight or branched alkyl group that has 1 to 3 carbon atoms. Examples of $C_{1-4}$ alkyl group are methyl, ethyl, propyl and isopropyl. $C_{1-3}$ alkyl group means straight or branched alkyl group that has 1 to 4 carbon atoms. Examples of $C_{1-3}$ alkyl groups are methyl, ethyl, propyl, isopropyl, butyl, isobutyl, and tert-butyl.

"Alkenyl" groups are straight chain, branch chain, and cyclic hydrocarbon groups containing at least one carbon-carbon double bond. Alkenyl groups can be substituted.

"Alkynyl" groups are straight chain, branch chain, and cyclic hydrocarbon groups containing at least one carbon-carbon triple bond. Alkynyl groups can be substituted.

An "alkoxy" group refers to an alklyl group linked to oxygen i.e. (alkyl)-O— group, where alkyl is as defined herein. Examples include methoxy (—$OCH_3$) or ethoxy (—$OCH_2CH_3$) groups.

An "alkenyloxy" group refers to an alkenyl group linked to oxygen i.e. (alkenyl)-O— group, where alkenyl is as defined herein.

An "alkynyloxy" group refers to an alkynyl group linked to oxygen i.e. (alkynyl)-O— group, where alkynyl is as defined herein.

An "aryloxy" group refers to an aryl group linked to oxygen i.e. (aryl)-O— group, where the aryl is as defined herein. An example includes phenoxy (—$OC_6H_5$) group.

"Silyl" refers to $H_3Si$—. "Substituted silyl" as used herein, refers to a moiety which has one or more the hydrogen of silyl substituted. Examples include, but are not limited to, TBDMS {tert-butyldimethylsilyl}, TBDPS (tert-butyldiphenylsilyl) or TMS {trimethylsilyl} group.

The term "halogen" is intended to include fluorine, chlorine, bromine and iodine. The term "halide" includes fluoride, bromide, iodide and chloride.

An "acyl protection group" comprises an acyl group —C(=O)—$R^7$, wherein $R^7$ is a terminal group, for example a group selected from, alkyl-, alkyl-, alkenyl-, alkynyl-, cycloalkyl- and aryl-group; or a group selected from, unsubstituted alkyl-, unsubstituted alkenyl-, unsubstituted alkynyl-, unsubstituted cycloalkyl- or unsubstituted aryl-group; or a group selected from substituted alkyl-, substituted alkenyl-, substituted alkynyl-, substituted cycloalkyl- or substituted aryl-group. In some embodiments $R^7$ may be selected from the group consisting of unsubstituted $C_{1-6}$-alkyl-, unsubstituted $C_{2-6}$-alkenyl-, unsubstituted $C_{3-7}$-cycloalkyl- or unsubstituted phenyl-group or substituted $C_{1-6}$-alkyl-, substituted $C_{2-6}$-alkenyl-, substituted $C_{2-6}$-alkinyl-, substituted $C_{3-7}$-cycloalkyl- or substituted phenyl-group; wherein when substituted, the substituent group may be mono or poly substituted, e.g. with one or more substituents selected from the group consisting of halogen, $C_{1-6}$-alkyl, $C_{2-6}$-alkenyl, $C_{2-6}$-alkynyl, $C_{1-6}$-alkoxy, optionally substituted aryloxy or optionally substituted aryl. In some embodiments the acyl protection group is isobuturyl (—C(O=)CH($CH_3$)$_2$) (also referred to herein as iBu). The term isobuturyl may also be spelt isobutyryl.

The invention provides a nucleoside monomer of formula 1, such as formula 1a or 1b, and a solvent composition (a solution) comprising the nucleoside monomer, and their use in the synthesis of an oligonucleotide.

The R and $R^1$ ($R/R^1$) groups of the nucleoside of formula 1a provide a stereocenter (L) which results in the formation of a Sp stereodefined phosphorothioate group 3' to the nucleoside when incorporated into an oligonucleotide. The monomer comprising the stereocenter created by the R and $R^1$ groups as shown in formula 1a is referred to as an L monomer herein which results in the formation of a Sp stereocenter. In some embodiments, the invention is based upon a surprising observation that DMF protected guanine L monomers, such as L-LNA-G monomers, are difficult to solubilize in many solvents, and even when solubilized are so unstable as to limit the ability to make stereodefined oligonucleotides to a commercially relevant scale. The problem is less severe for L-DNA-G monomers as compared to sugar modified nucleosides, such as bicyclic nucleosides, such as L-LNA-G nucleosides. Indeed a side by side comparison of the solubility of DMF protected L-LNA-G and D-LNA-G (where the stereochemistry of the stereocenters R/$R^1$ and $R^6$/$R^9$ of formula 1 is reversed as shown in formula 1b), shows that whereas the DMF protected D-LNA-G is soluble and stable in most solvents, the DMF protected L-LNA-G is very difficult to solubilise and has a stability in solution of less than 24 hours.

The R and $R^1$ ($R/R^1$) groups of the nucleoside of formula 1b provide a stereocenter (D) which results in the formation of a Rp stereodefined phosphorothioate group 3' to the nucleoside when incorporated into an oligonucleotide. The monomer comprising the stereocenter created by the R and $R^1$ groups as shown in formula 1b is referred to as an D monomer herein which results in the formation of a Rp stereocenter.

Mixtures of Diastereoisomers

The invention provides a composition which comprises the compound of formula 1a. In some embodiments, said composition does not comprise the compound of formula 1b. In some embodiments, the composition does not comprise more that 1% of the compound of formula 1b (as measured by molar ratio of the compound of formula 1a). In some embodiments, the composition does not comprise more that 2% of the compound of formula 1b (as measured by molar ratio of the compound of formula 1a). In some embodiments, the composition does not comprise more that 3% of the compound of formula 1b (as measured by molar ratio of the compound of formula 1a). In some embodiments, the composition does not comprise more that 4% of the compound of formula 1b (as measured by molar ratio of the compound of formula 1a). In some embodiments, the composition does not comprise more that 5% of the compound of formula 1b (as measured by molar ratio of the compound of formula 1a). In some embodiments, the composition does not comprise more that 10% of the compound of formula 1b (as measured by molar ratio of the compound of formula 1a). In some embodiments, the composition does not comprise more that 20% of the compound of formula 1b (as measured by molar ratio of the compound of formula 1a). The composition may be in the form of the solution (composition) as described herein.

The invention provides a composition which comprises the compound of formula 1b. In some embodiments, said composition does not comprise the compound of formula 1a. In some embodiments, the composition does not comprise more that 1% of the compound of formula 1a (as measured by molar ratio of the compound of formula 1b). In some embodiments, the composition does not comprise more that 2% of the compound of formula 1a (as measured by molar ratio of the compound of formula 1b).

In some embodiments, the composition does not comprise more that 3% of the compound of formula 1a (as measured by molar ratio of the compound of formula 1b). In some embodiments, the composition does not comprise more that 4% of the compound of formula 1a (as measured by molar ratio of the compound of formula 1b). In some embodiments, the composition does not comprise more that 5% of the compound of formula 1a (as measured by molar ratio of the compound of formula 1b). In some embodiments, the composition does not comprise more that 10% of the compound of formula 1a (as measured by molar ratio of the compound of formula 1b). In some embodiments, the composition does not comprise more that 20% of the compound of formula 1a (as measured by molar ratio of the compound of formula 1b). The composition may be in the form of the solution (composition) as described herein.

L-Monomers

In some embodiments, the invention provides for a compound of formula 1a

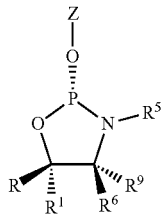

Formula 1a wherein

Z is a guanine nucleoside wherein the guanine nucleobase group comprises an acyl protection group on the guanine exocyclic nitrogen group, wherein the exocyclic oxygen of Formula 1a is covalently attached to the 3' carbon of the nucleoside Z;

$R^5$ and $R^6$ are independently selected from the group consisting of hydrogen, alkyl, cyclo-alkyl, aryl, heteroaryl, substituted alkyl, substituted cyclo-alkyl, substituted aryl, and substituted heteroaryl, or $R^5$ and $R^6$ together form a heterocyclic ring comprising 3-16 carbon atoms, together with the N atom of formula 1a;

$R^9$ is hydrogen;

$R^1$ is selected from the groups consisting of hydrogen and $C_{1-3}$ alkyl; and, R is selected from the groups consisting of aryl, heteroaryl, substituted aryl, substituted heteroaryl, nitro, halogen, cyano, silyl, substituted silyl, sulfone, substituted sulfone (aryl substituted sulfone), fluorene, and substituted fluorene.

The description of the groups R, $R^1$, $R^6$, $R^9$ and $R^5$ herein may apply generally to the compounds described here, including both L and D stereoisoforms.

When substituted, R may be substituted with a group selected from the group consisting of: $C_{1-4}$ alkyl group, $C_{6-14}$ aryl group $C_{1-4}$, alkoxy group, $C_{7-14}$ aralkyl group, $C_{1-4}$ alkyl, $C_{6-14}$ aryl group, $C_{1-4}$ alkoxy, $C_{6-14}$ aryl group, or $C_{6-14}$ aryl $C_{1-4}$ alkyl group. Multiple substitutions may be dependently or independently selected from the group consisting of: $C_{1-4}$ alkyl group, $C_{6-14}$ aryl group $C_{1-4}$, alkoxy group, $C_{7-14}$ aralkyl group, $C_{1-4}$ alkyl, $C_{6-14}$ aryl group, $C_{1-4}$ alkoxy, $C_{6-14}$ aryl group, or $C_{6-14}$ aryl $C_{1-4}$ alkyl group.

In some embodiments R is selected from the groups consisting of aryl, heteroaryl, substituted aryl, substituted heteroaryl, nitro, halogen, cyano, silyl, substituted silyl, sulfone, substituted sulfone (aryl substituted sulfone), fluorene, and substituted fluorene.

In some embodiments R is selected from the group consisting of aryl, heteroaryl, substituted aryl and substituted heteroaryl.

In some embodiments R is aryl, such as phenyl.

In some embodiments, when R is substituted aryl, R may be substituted with halide, such as iodide, fluoride, bromide or chloride, such as phenyl substituted with halide, such as iodide, fluoride, bromide or chloride.

In some embodiments $R^1$ is hydrogen. In some embodiments $R^1$ is $C_{1-3}$ alkyl, such as methyl, ethyl or propyl. In some embodiments $R^1$ is methyl.

In some embodiments, R is aryl, such as phenyl and $R^1$ is hydrogen.

In some embodiments, R is aryl, such as phenyl, and $R^1$ is $C_{1-3}$ alkyl, such as methyl, ethyl or propyl.

In some embodiments R is

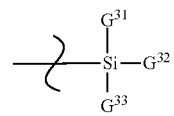

wherein $G^{31}$, $G^{32}$ and $G^{33}$ are independently selected from the groups consisting of $C_{1-4}$ alkyl, $C_{6-14}$ aryl$C_{1-4}$ alkoxy, $C_{7-14}$ aralkyl, $C_{1-4}$ alkyl$C_{6-14}$ aryl, $C_{1-4}$ alkoxy$C_{6-14}$ aryl, and $C_{6-14}$ aryl$C_{1-4}$ alkyl.

In some embodiments R is

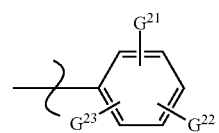

wherein $G^{21}$, $G^{22}$ and $G^{23}$ are independently hydrogen, nitro, halogen, cyano or $C_{1-3}$ alkyl.

In some embodiments R is

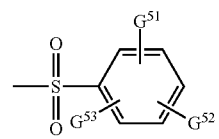

wherein $G^{51}$, $G^{52}$ and $G^{53}$ are independently hydrogen, nitro, halogen, cyano or $C_{1-3}$ alkyl or $C_{1-3}$ alkyloxy group.

In some embodiments $R^5$ and $R^6$ together form a heterocylic ring (with the cyclic nitrogen shown in Formula 1). The heterocyclic ring may comprise, for example 3-16 carbon atoms, such as 4 carbons atoms.

In some embodiments $R^5$ and $R^6$ together form a heterocylic ring (with the cyclic nitrogen shown in Formula I) which comprises 4 carbon atoms, making a total of five atoms in the heterocyclic ring (4 carbon and the nitrogen shown in Formula 1). For example, the compound of the invention may be of formula 2:

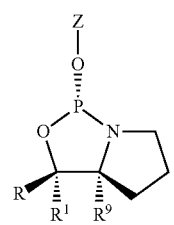

Formula 2

Wherein R, $R^1$, $R^9$ and Z are as according to the compound of the invention.

In some embodiments $R^5$ and $R^6$ together form a heterocylic ring (with the cyclic nitrogen shown in Formula I) which comprises 4 carbon atoms, making a total of five atoms in the heterocyclic ring (4 carbon and the nitrogen shown in Formula 1), and R is aryl, such as phenyl, $R^1$ is hydrogen or methyl. $R^9$ is hydrogen.

The Z group above is a nucleoside where the 3' oxygen of the nucleoside is the exocyclic oxygen shown in formula 1. In some embodiments the Z group is a LNA nucleoside moiety. In some embodiment the compound of the invention may therefore be represented as the compound of formula 3:

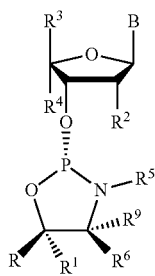

Formula 3 wherein, R, $R^1$, $R^5$, $R^6$ and $R^9$ are as per the compound of the invention;

B is the guanine nucleobase group comprising an acyl protecting group on the guanine exocyclic nitrogen group;

$R^3$=is selected from the group consisting of $CH_2ODMTr$, $CH_2$-Alkyl-O-DMTr, CH-Me-O-DMTr, $CH_2OMMTr$, $CH_2$-Alkyl-O-MMTr, CH(Me)-O-MMTr, CH—$R^a$—O-DMTr$R^b$, and CH—$R^a$—O-MMTr$R^b$;

$R^2$ is selected from the groups consisting of halo, such as —F, amino, azido, —SH, —CN, —OCN, —$CF_3$, —$OCF_3$, —O($R'''$)-alkyl, —S($R'''$)-alkyl, —N($R'''$)-alkyl, —O($R'''$)-alkenyl, —S($R'''$)-alkenyl, —N($R'''$)-alkenyl; —O($R'''$)-alkynyl, —S($R'''$)-alkynyl or —N($R'''$)-alkynyl; O-alkylenyl-O-alkyl, alkynyl, alkaryl, aralkyl, O-alkaryl, O-aralkyl, $O(CH_2)_2SCH_3$, O—$(CH_2)_2$—O—N($R'''$)($R''$) or O—$CH_2$C(=O)—N($R'''$)($R''$), —O—$(CH_2)_2OCH_3$, and —O—$CH_3$, where each $R'''$ and $R''$ are independently, H, an amino protecting group or substituted or unsubstituted $C_{1-10}$ alkyl;

$R^4$=is selected from the group consisting of alkyl, cyclo-alkyl, cyclo-heteroalkyl, O-alkyl, S-alkyl, NH-alkyl, and hydrogen;

or $R^2$ and $R^4$ together designate a bivalent bridge, such as consisting of 1, 2, 3 groups/atoms selected from the group consisting of —C($R^aR^b$)—, —C($R^a$)=C($R^b$), —C($R^a$)=N, O, —Si($R^a$)2-, S—, —$SO_2$—, —N($R^a$)—, and >C=Z;

wherein $R^a$ and, when present $R^b$, each is independently selected from hydrogen, optionally substituted $C_{1-6}$-alkyl, optionally substituted $C_{2-6}$-alkenyl, optionally substituted $C_{2-6}$-alkynyl, hydroxy, optionally substituted $C_{1-6}$-alkoxy, $C_{2-6}$-alkoxyalkyl, $C_{2-6}$-alkenyloxy, carboxy, $C_{1-6}$-alkoxycarbonyl, $C_{1-6}$-alkylcarbonyl, formyl, aryl, aryl¬oxy-carbonyl, aryloxy, arylcarbonyl, heteroaryl, hetero¬aryloxy-carbonyl, heteroaryloxy, heteroarylcarbonyl, amino, mono- and di($C_{1-6}$-alkyl)amino, carbamoyl, mono- and di($C_{1-6}$-alkyl)-aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkyl-thio, halogen, where aryl and heteroaryl may be optionally substituted and where two geminal substituents $R^a$ and $R^b$ together may designate optionally substituted methylene (=$CH_2$), wherein for all chiral centers, asymmetric groups may be found in either R or S orientation.

In some embodiments, when incorporated into an oligo-nucleotide, the nucleoside (Z) confers a higher binding affinity to a complementary RNA target than an equivalent DNA nucleoside. Such nucleosides are referred to as high affinity nucleosides. Examples of high affinity nucleosides include 2'-O-MOE, 2'-fluoro, 2'-O-methyl, and LNA nucleosides. In the embodiments, where the nucleoside is a high affinity nucleoside $R^3$ may, for example be $CH_2$—O-DMTr or $CH_2$—O-MMTr.

In some embodiments, $R^2$ is selected from the group consisting of fluoro (—F), —O—$(CH_2)_2OCH_3$, and —O—$C_{1-3}$ alkyl, such as —O—$CH_3$. In such embodiments, optionally $R^4$ is hydrogen.

In some embodiments, the nucleoside is a LNA nucleoside (also known as a bicyclic nucleoside) comprising a 2'-4' bridge (biradicle).

In some embodiments, $R^2$ and $R^4$ together designate a bivalent bridge selected from the group consisting of bridge —C($R^aR^b$)—O—, —C($R^aR^b$)C($R^aR^b$)—O—, —$CH_2$—O—, —$CH_2CH_2$—O—, —CH($CH_3$)—O—. In some embodiments, $R^2$ and $R^4$ designate the bivalent bridge —$CH_2$—O— (methylene-oxy also known as oxy-LNA) or —CH($CH_3$)—O— (methyl-methylene-oxy). The —CH($CH_3$)—O— bridge introduces a chiral center at the carbon atom within the bridge, in some embodiments this is in the S position (for example a nucleoside known in the art as (S)cET—see EP1984381)). In some embodiments, $R^2$ and $R^4$ designate the bivalent bridge —$CH_2$—O— wherein the bridge is in the beta-D position (beta-D-oxy LNA). In some embodiments, $R^2$ and $R^4$ designate the bivalent bridge —$CH_2$—O— wherein the bridge is in the alpha-L position (alpha-L-D-oxy LNA). In some embodiments, $R^2$ and $R^4$ designate the bivalent bridge —$CH_2$—S— (thio LNA), or —$CH_2$—$NH_2$— (amino LNA). In the embodiments where $R^2$ and $R^4$ together designate a bivalent bridge, $R^3$ may, for example be $CH_2$—O-DMTr or $CH_2$—O-MMTr. In some embodiments where the nucleoside (Z) is a bicyclic nucleotides (LNA) such as beta-D-oxy LNA, R is aryl, such as phenyl, and $R^1$ is hydrogen or $C_{1-3}$ alkyl. In such am embodiment, $R^5$ and $R^6$ may together form a heterocyclic ring, such as a five membered heterocyclic ring, as described herein (e.g. see formula 2).

The compound of the invention comprises an acyl protected guanine nucleoside (Z).

The compound of the invention may, in some embodiments, be represented by a compound of formula 10, 11, 12, 13, 14, 15, 16, 17, 18, 19, 20, 21, 22, 23 24, or 25:

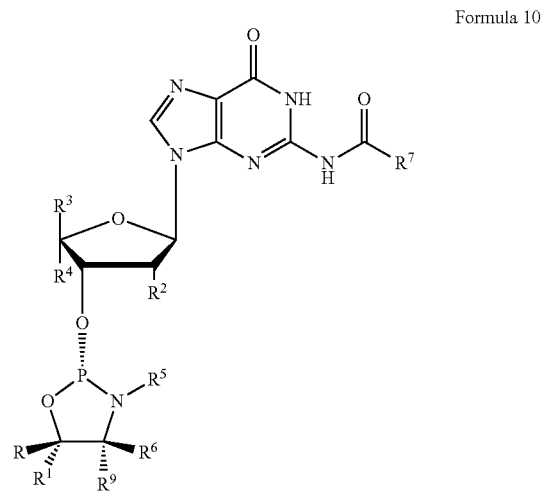

Formula 10

Formula 11
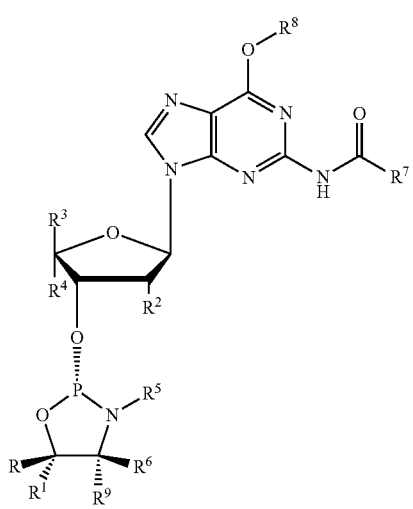
Formula 12
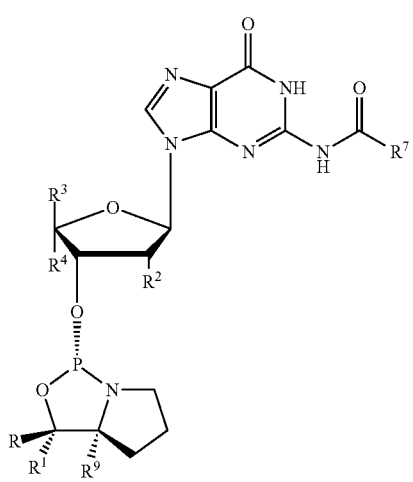
Formula 13
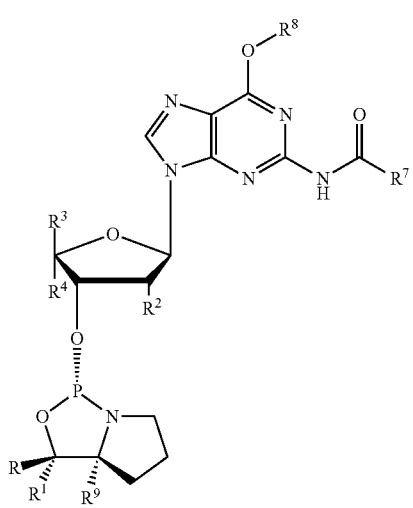
Formula 14
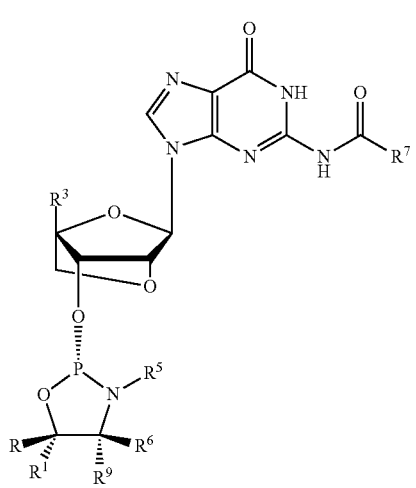
Formula 15
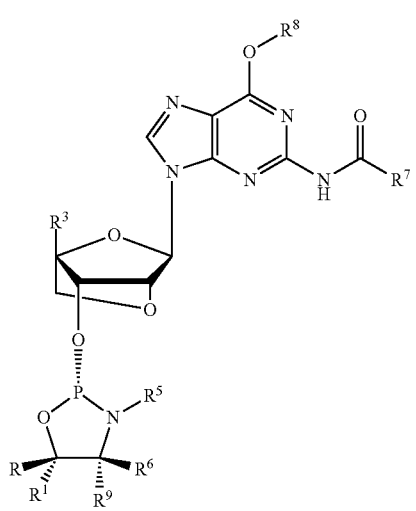
Formula 16
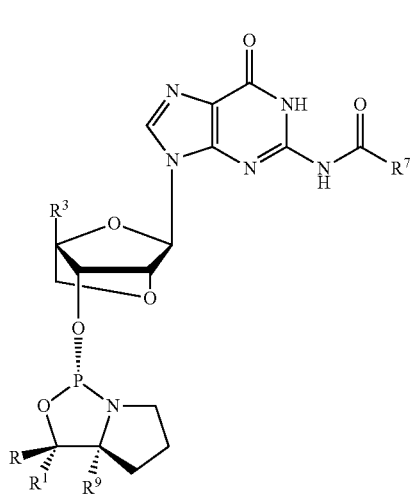

Formula 17
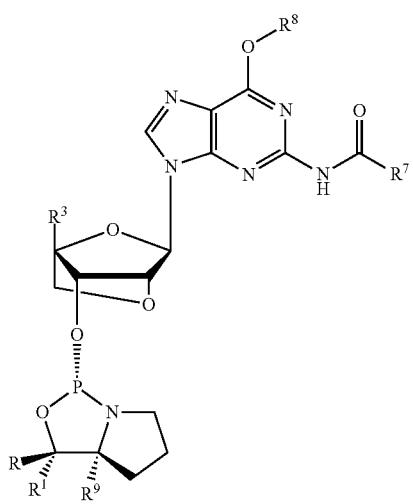
Formula 20
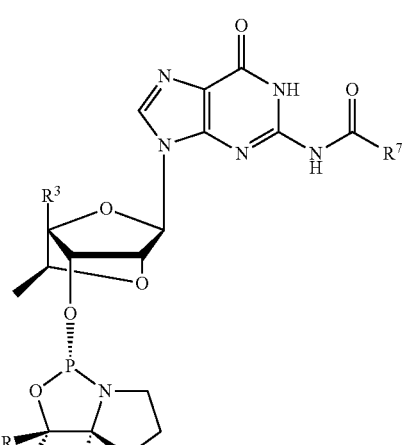
Formula 18
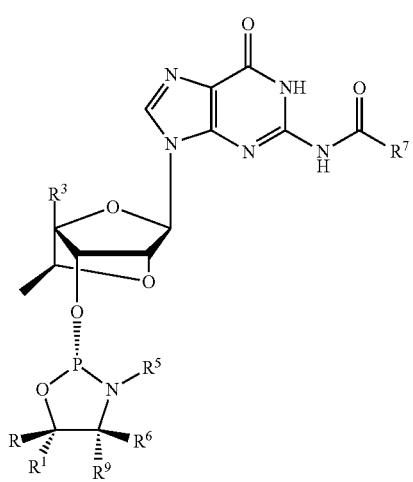
Formula 21
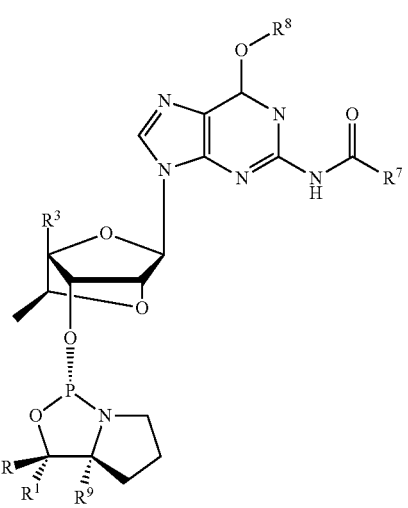
Formula 19
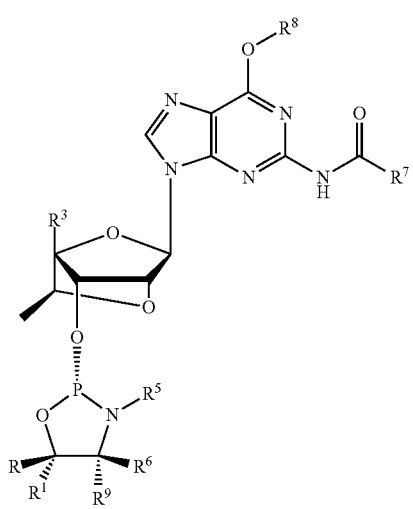
Formula 22
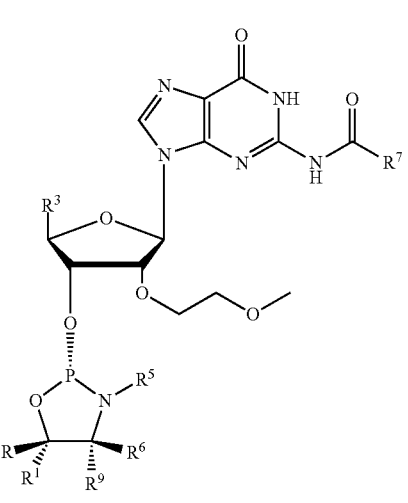

Formula 23
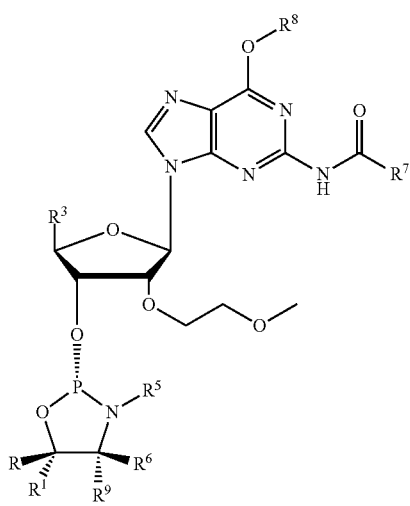
Formula 24
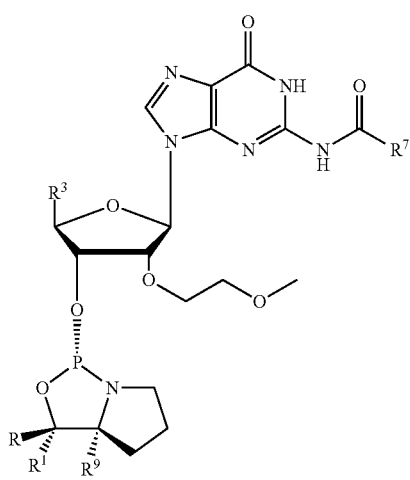
Formula 25
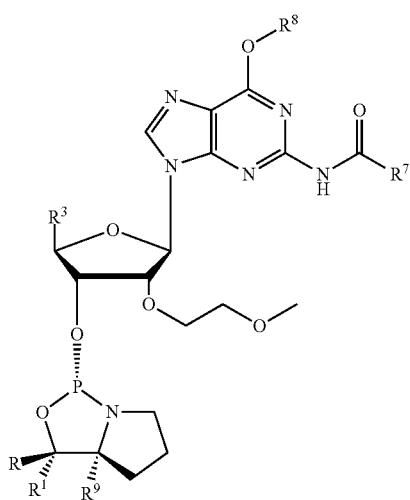
Formula 26
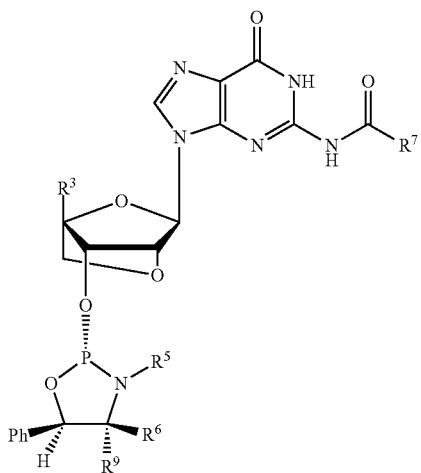
Formula 27
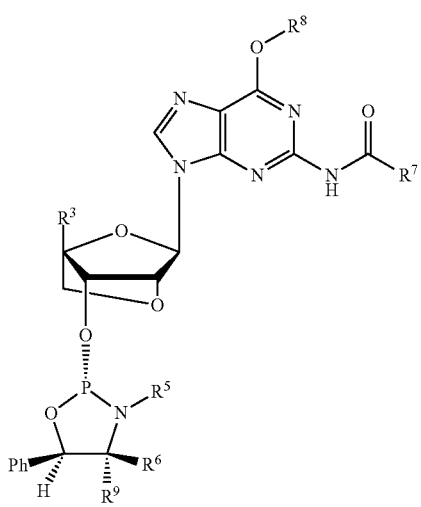
Formula 28
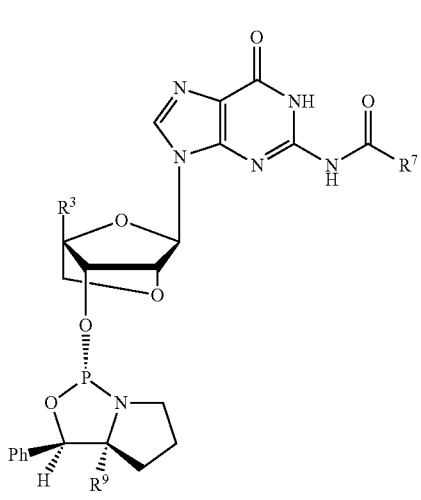

Formula 29
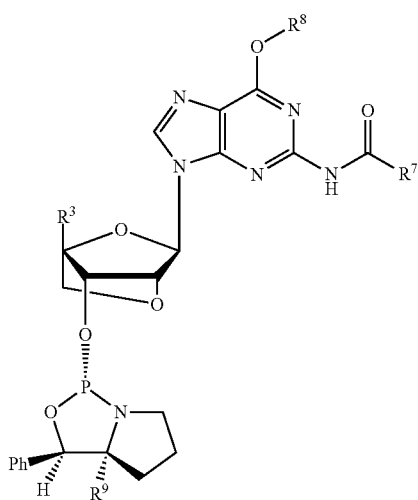
Formula 30
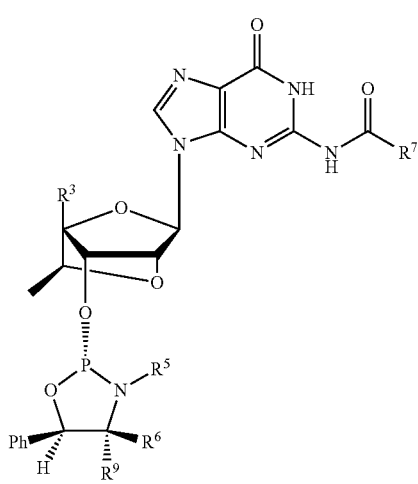
Formula 31
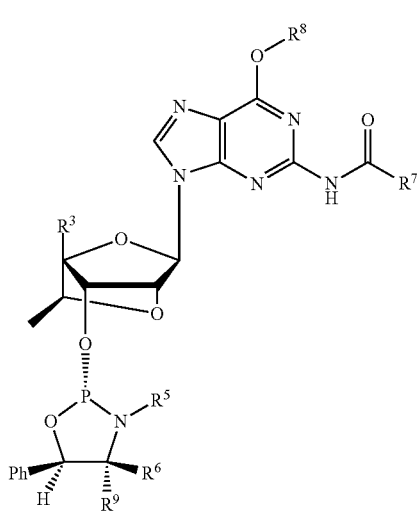
Formula 32
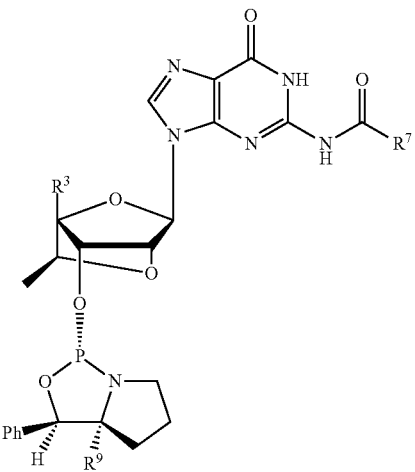
Formula 33
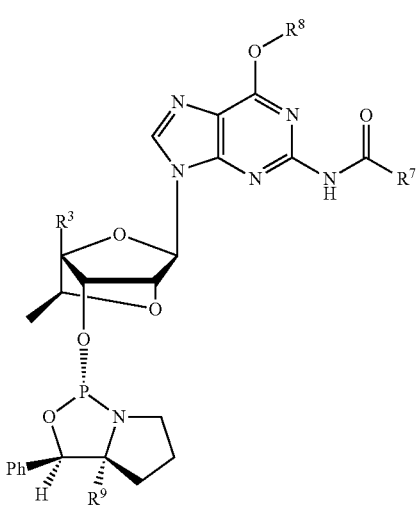
Formula 34
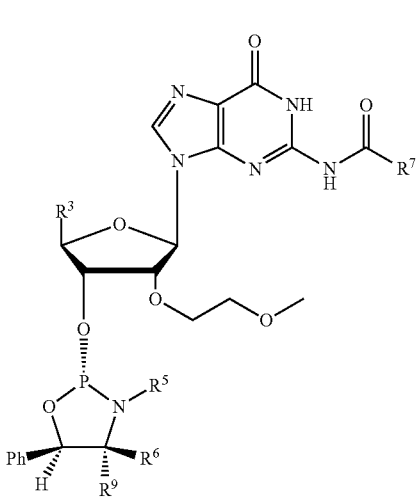

-continued
Formula 35
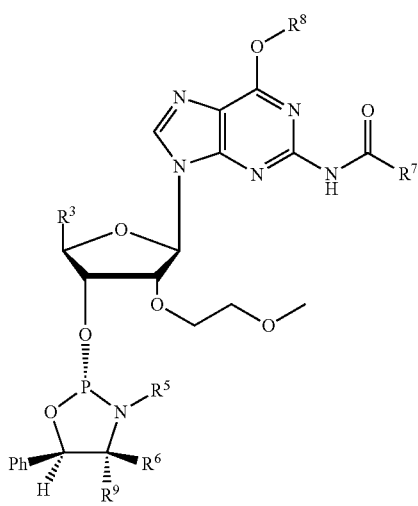
Formula 36
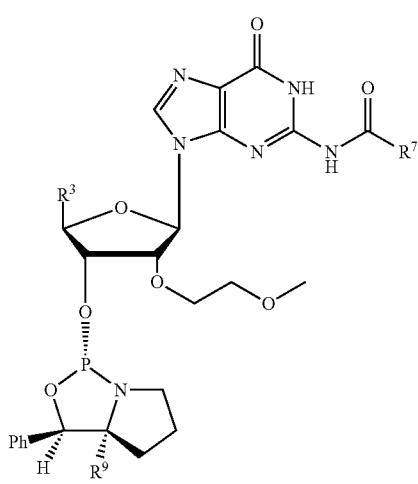
Formula 37
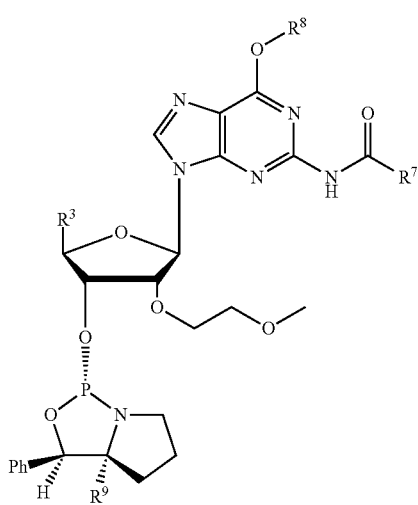
-continued
Formula 38
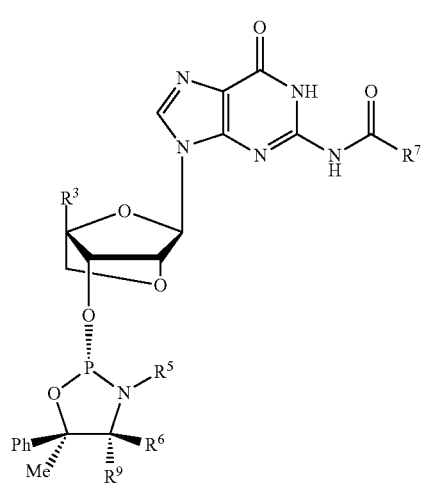
Formula 39
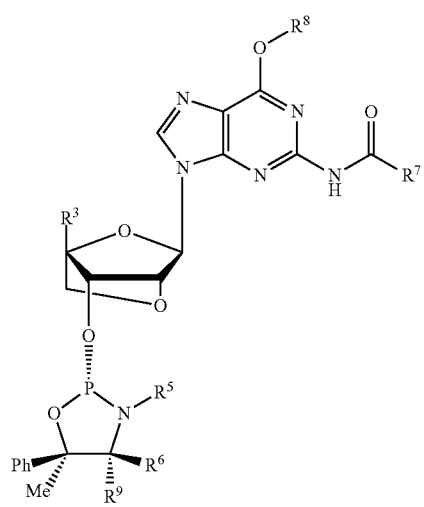
Formula 40
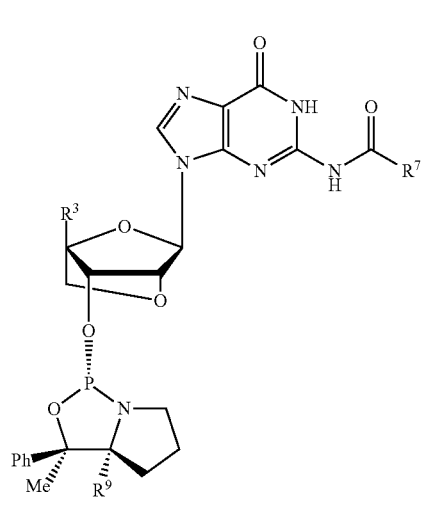

Formula 41
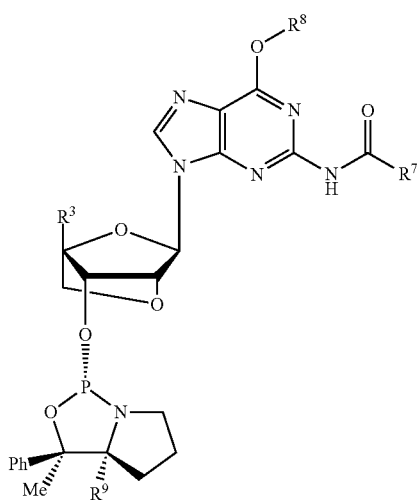
Formula 42
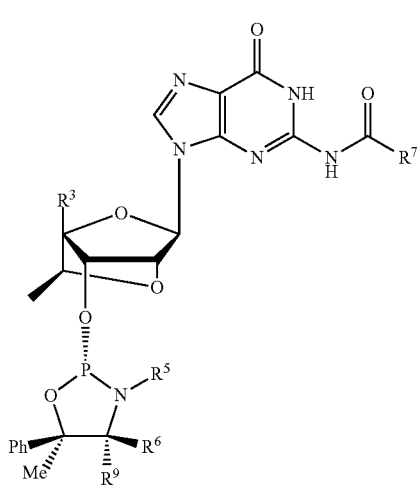
Formula 43
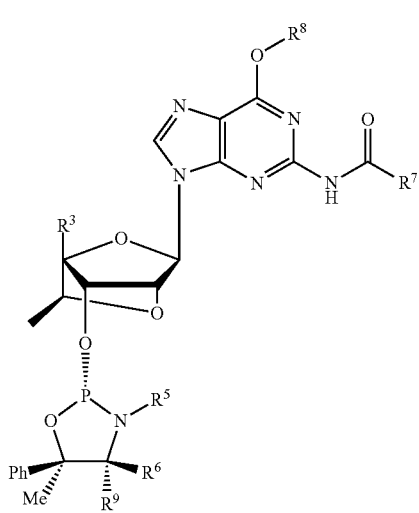
Formula 44
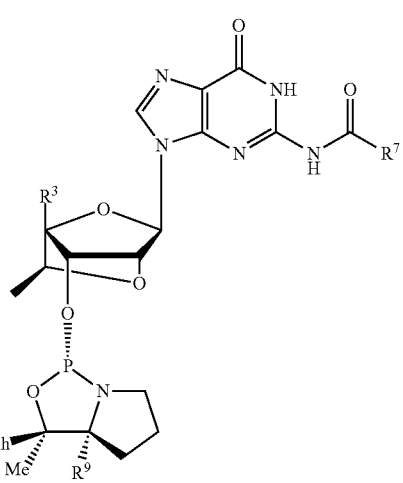
Formula 45
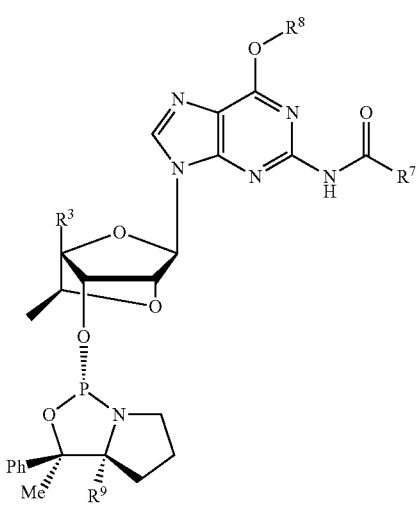
Formula 46
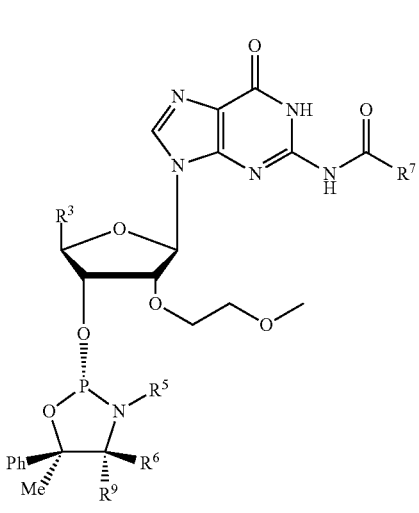

-continued

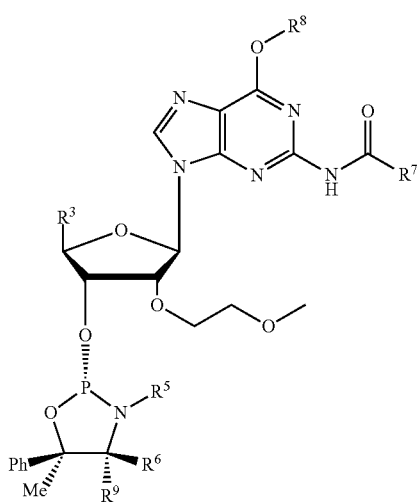

Formula 47

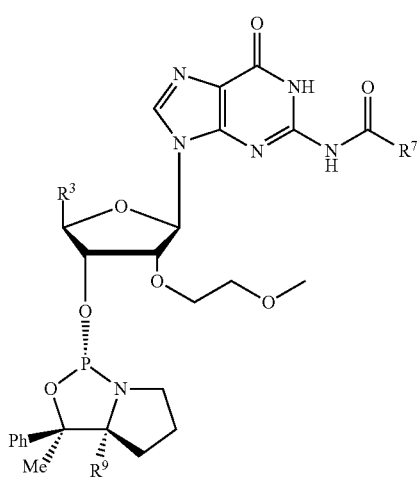

Formula 48

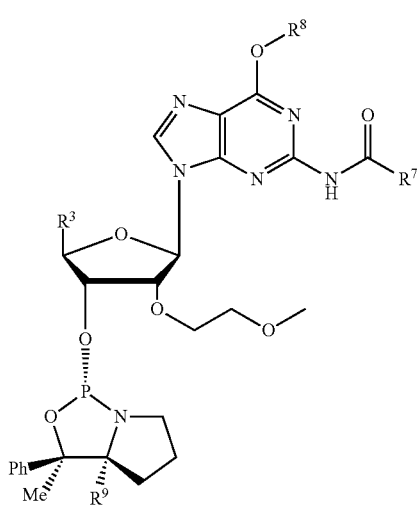

Formula 49 wherein, R, $R^1$, $R^2$, $R^3$, $R^4$, $R^5$, $R^9$ and $R^6$ are as per the compound of the invention, and —C(=O)—$R^7$ is the acyl protecting group on the exocyclic nitrogen of the guanine base, and $R^8$ when present is a protecting group on the guanine exocyclic oxygen. In some embodiments $R^8$ is cyanoethyl. In some embodiments, $R^9$ is hydrogen.

In some embodiments of the compound of the invention, $R^7$ is selected from the group consisting of optionally substituted alkyl-, alkenyl-, alkynyl-, cycloalkyl- or aryl-group, preferably from an optionally substituted $C_{1-6}$-alkyl-, $C_{2-6}$-alkenyl-, $C_{2-6}$-alkinyl-, $C_{3-7}$-cycloalkyl- or phenyl-group; wherein when substituted, the substituent group may be mono or poly substituted, e.g. with one or more substituents selected from the group consisting of halogen, $C_{1-6}$-alkyl, $C_{2-6}$-alkenyl, $C_{2-6}$-alkynyl, $C_{1-6}$-alkoxy, optionally substituted aryloxy or optionally substituted aryl. In some embodiments alkyl is branched alkyl, such as $C_{3-10}$ or $C_{3-6}$ branched alkyl.

In some embodiments $R^7$ is a branched alkyl, such as a substituted or unsubstituted branched alkyl, such as, iso-propyl, iso-butyl, sec-butyl, and tert-butyl. In some embodiments $R^7$ is iso-propyl.

In some embodiments, the acyl protecting group (e.g. —C(=O)—$R^7$) on the guanine exocyclic nitrogen group, is selected from the group consisting of isobuturyl (iBu), Acetyl (Ac), Phenoxyacetyl (PAC), p-Isopropylphenoxyacetyl (iPrPAC), phenylacetyl, Isopropyloxyacetyl, methoxyacetyl, benzoyl, p-methoxyphenylacetyl, diphenylacetyl, cyclohexylcarbonyl, 1,1-dimethylpropanoyl, and p-tert-Butyl-phenoxyacetyl.

In some embodiments, the acyl protecting group on the guanine exocyclic nitrogen group is selected from the group consisting of isobuturyl (iBu), Acetyl (Ac), phenoxyacetyl (PAC), and p-Isopropylphenoxyacetyl (iPrPAC).

In some embodiments the acyl protecting group on the guanine exocyclic nitrogen group is an isobuturyl (iBu) terminal group In the embodiments where $R^2$ and $R^4$ together designate a bivalent bridge, $R^3$ may be $CH_2$—O-DMTr or $CH_2$—O-MMTr, and the acyl protecting group (e.g. —C(=O)—$R^7$) on the guanine exocyclic nitrogen group is isobuturyl (iBu), R may be phenyl, and $R^1$ may be either hydrogen or methyl, and $R^5$ and $R^6$ together form a five membered heterocycle, such as that shown in formula 2.

The compound of the invention may, in some embodiments, be represented by a compound of formula 50, 51, 52, 53, 54, 55, 56, 57, 58, 59, 60 or 61:

Formula 50

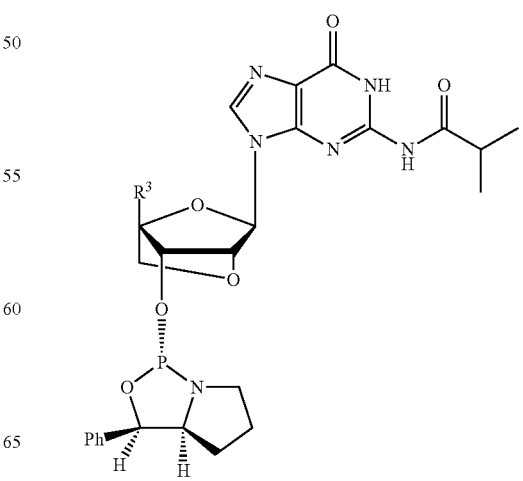

-continued
Formula 51
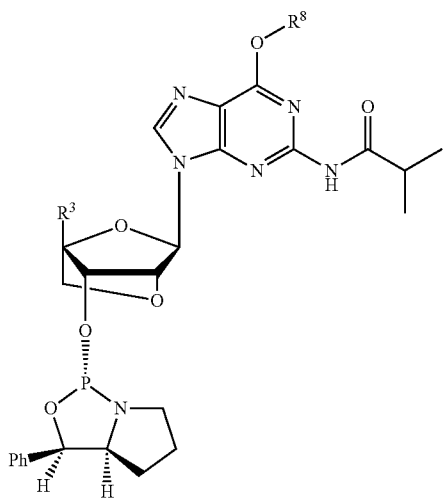
Formula 52
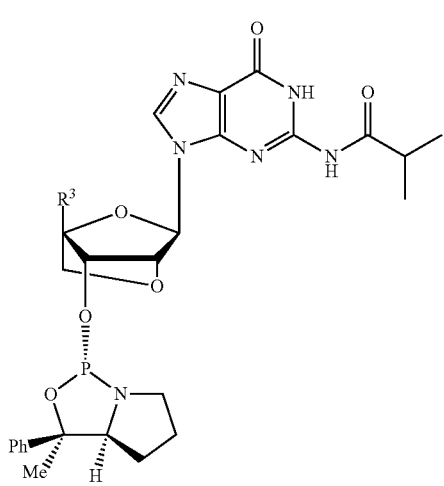
Formula 53
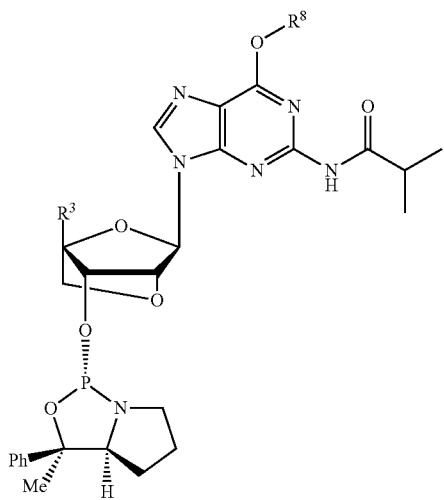
-continued
Formula 54
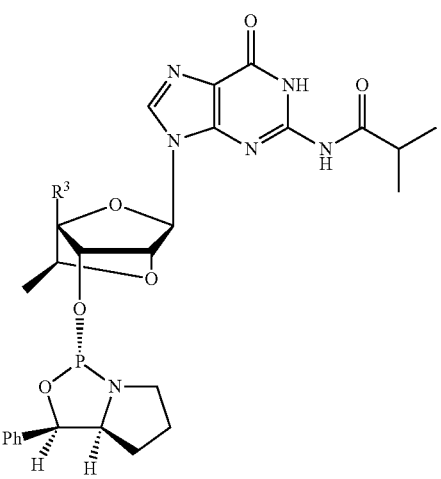
Formula 55
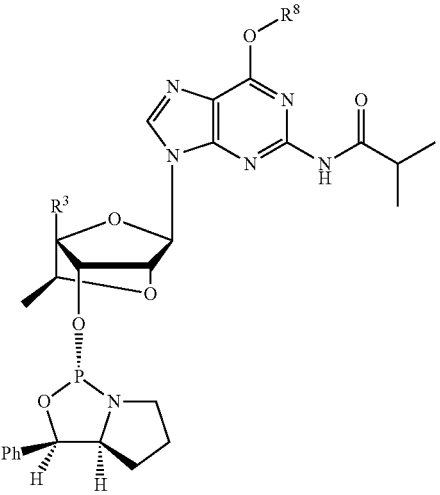
Formula 56
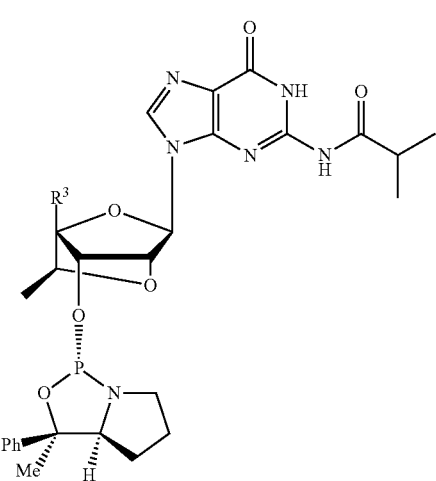

Formula 57

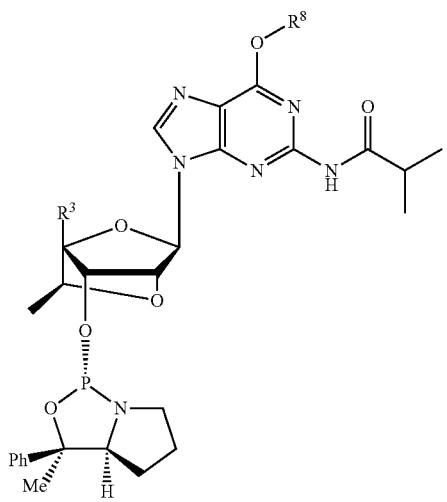

Formula 58

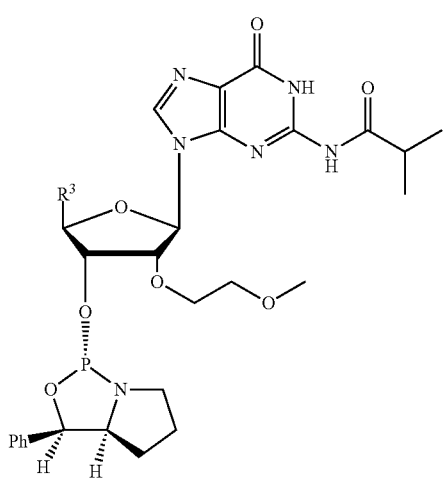

Formula 59

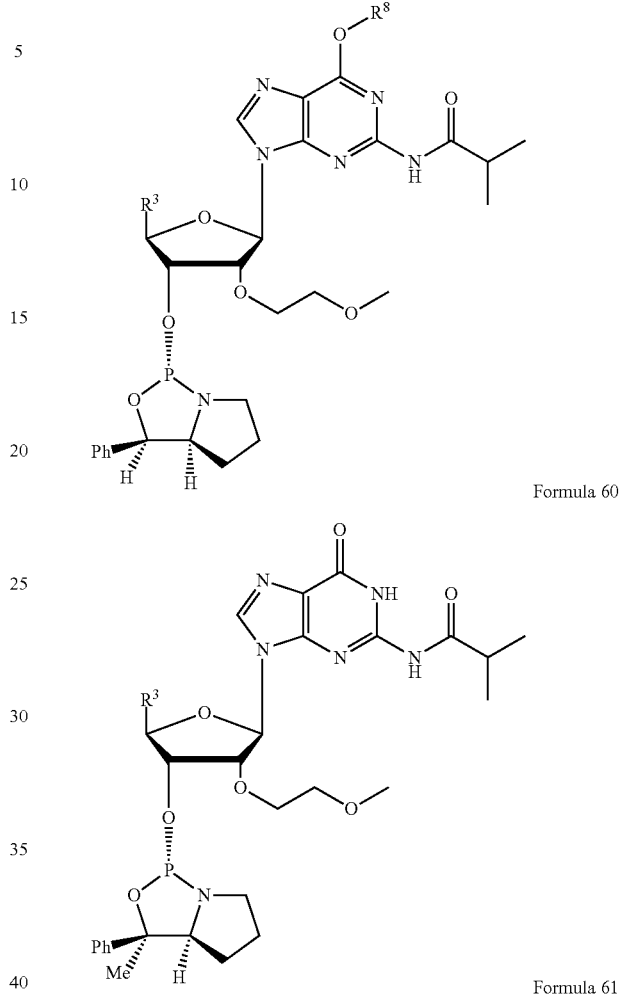

Formula 60

Formula 61 wherein R³ and R⁸ (when present) are as per the compound of the invention. In some embodiments, R³ is selected from the group consisting of CH₂ODMTr, CH₂-Alkyl-O-DMTr, CH-Me-O-DMTr, CH₂OMMTr, CH₂-Alkyl-O-MMTr, CH(Me)-O-MMTr, CH—R$^a$—O-DMTrR$^b$, and CH—R$^a$—O-MMTrR$^b$, and R⁸ (when present) may be cyanoethyl; wherein R$_a$ and R$_b$ are as per the compound of the invention.

In some embodiments, the invention provides a compound according to any one of formulas 75, 76 and 77:

Formula 75

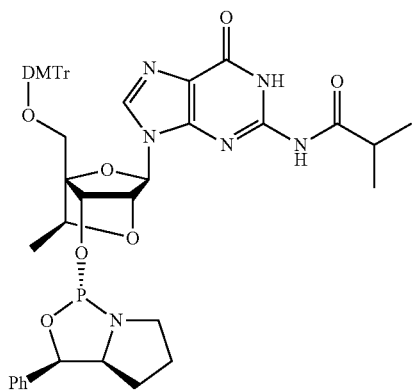

N-(9-(((1S,3R,4R,6S,7S)-1-((bis(4-methoxyphenyl)(phenyl)methoxy)methyl)-6-methyl-7-(((1R,3R,3aS)-3-phenyltetrahydro-1H,3H-pyrrolo[1,2-c][1,3,2]oxazaphosphol-1-yl)oxy)-2,5-dioxabicyclo[2.2.1]heptan-3-yl)-6-oxo-6,9-dihydro-1H-purin-2-yl)isobutyramide Formula 76

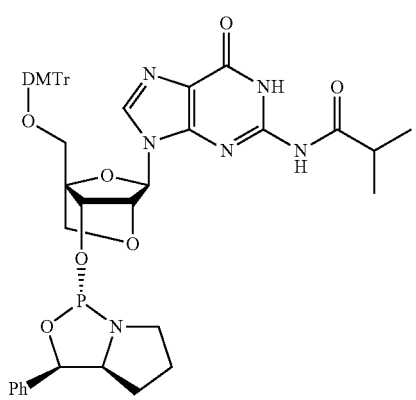

N-(9-((1R,3R,4R,7S)-1-((bis(4-methoxyphenyl)(phenyl)methoxy)methyl)-7-(((1R,3R,3aS)-3-phenyltetrahydro-1H,3H-pyrrolo[1,2-c][1,3,2]oxazaphosphol-1-yl)oxy)-2,5-dioxabicyclo[2.2.1]heptan-3-yl)-6-oxo-6,9-dihydro-1H-purin-2-yl)isobutyramide Formula 77

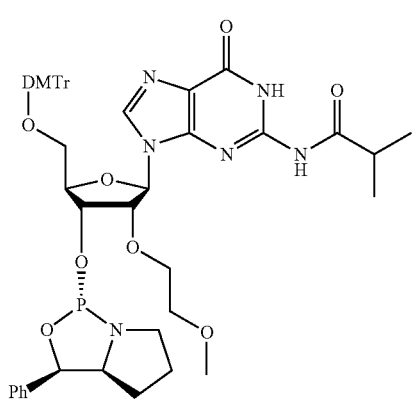

N-(9-((2R,3R,4R,5R)-5-((bis(4-methoxyphenyl)(phenyl)methoxy)methyl)-3-(2-methoxyethoxy)-4-(((1R,3R,3aS)-3-phenyltetrahydro-1H,3H-pyrrolo[1,2-c][1,3,2]oxazaphosphol-1-yl)oxy)tetrahydrofuran-2-yl)-6-oxo-6,9-dihydro-1H-purin-2-yl)isobutyramide It will be recognised that in some embodiments the compounds of formula 75, 76 and 77 may have $R^1$ group which is methyl (rather than hydrogen).

Solvent Compositions

The invention provides for a solvent composition comprising the compound of the invention and a solvent, such as a polar aprotic solvent. Suitably the compound of the invention is soluble in the solvent. The invention therefore provides for a solution comprising the compound of the invention. The solution may be a stable solution. A stable solution, i.e. the compound of the invention is soluble in the solvent and is stable for at least 24 hours at room temperature (e.g. 20° C.). The examples provide methods for determining the solubility and stability of solution compositions comprising the compounds of the invention.

In some embodiments, the stability of the compound of the invention in the solution (e.g. solution composition), is at least about 20%, such as at least about 30%, such as at least about 40%, such as at least about 50%, such as at least about 60%, such as at least about 70%, such as at least about 75%, as measured after 24 hours using the Stability Determination Assay provided in Example 6 (typically performed at room temperature, such as 20-25° C.). Such solutions comprising the compound of the invention dissolved in solution which show stability after 24 hours (i.e. the amount of remaining compound after 24 hours as measured using the stability determination assay of example 6 is at least about 20%, such as at least about 30%, such as at least about 40%, such as at least about 50%, such as at least about 60%, such as at least about 70%, such as at least about 75%), are referred to as stable solutions herein. In some embodiments the invention provides a stable solution comprising the compound of the invention and a solvent, such as those referred to herein.

In some embodiments the solvent is a polar solvent. In some embodiments the solvent is an aprotic solvent.

In some embodiments, the solvent is or comprises a solvent selected from the group consisting of acetonitrile, DMF, DMSO, dioxane, tetrahydrofuran, dichloromethane, and dichloroethane.

In some embodiments, the solvent is or comprises acetonitrile or dioxane.

In some embodiments, the solvent comprises acetonitrile and acetone, for example in about 1:1 ratio.

In some embodiments, the solvent is or comprises DMSO or DMF.

In some embodiments, the solvent is or comprises tetrahydrofuran.

In some embodiments, the solvent is or comprises dichloromethane, or dichloroethane.

In some embodiments the solvent is other than toluene. In some embodiments, the solvent does not comprise toluene.

In some embodiments the solvent is other than DMSO or DMF. In some embodiments, the solvent does not comprise DMSO or DMF.

Method of Synthesis of Compounds of the Invention

The invention provides for a method of synthesis of the compound of the invention said method comprising the step of reacting a guanine nucleoside (Z) comprising a 3'—OH group; with a compound of formula 4:

Formula 4

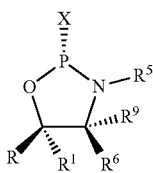

wherein X is halo, such as bromide, chloride or iodide, and wherein R, $R^1$, $R^5$, $R^6$ and $R^9$ are as according to the compound of the invention;

and wherein the guanine nucleobase group on the guanine nucleoside comprises an acyl protecting group on the guanine exocyclic nitrogen group, such as the acyl protecting group —C(=O)—$R^7$.

In some embodiments, the compound for formula 4 is selected from the group consisting of formula 5, 6, 7 and 8:

Formula 5

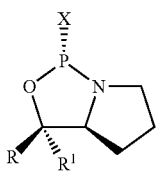

Formula 6

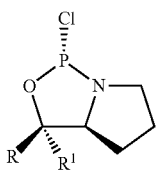

Formula 7

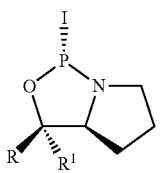

Formula 8

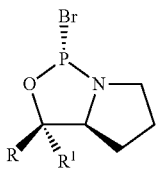

Wherein X is halo, such as chloride, bromide or iodide

In some embodiments X of formula 4 or 5 is chloride. The following may optionally apply to compounds of formula 4, 5, 6, 7 and 8:

In some embodiments R is selected from the groups consisting of aryl, heteroaryl, substituted aryl, substituted heteroaryl, nitro, halogen, cyano, silyl, substituted silyl, sulfone, substituted sulfone (aryl substituted sulfone), fluorene, and substituted fluorene.

In some embodiments R is selected from the group consisting of aryl, heteroaryl, substituted aryl and substituted heteroaryl.

In some embodiments R is aryl, such as phenyl.

In some embodiments, when R is substituted aryl, R may be substituted with halide, such as iodide, fluoride, bromide or chloride, such as phenyl substituted with halide, such as iodide, fluoride, bromide or chloride.

In some embodiments $R^1$ is hydrogen. In some embodiments $R^1$ is $C_{1-3}$ alkyl, such as methyl, ethyl or propyl. In some embodiments $R^1$ is methyl.

In some embodiments, R is aryl, such as phenyl and $R^1$ is hydrogen.

In some embodiments, R is aryl, such as phenyl, and $R^1$ is $C_{1-3}$ alkyl, such as methyl, ethyl or propyl.

In some embodiments, R is phenyl, $R^1$ is hydrogen, X is bromine, and $R^5$ and $R^6$ together form a five membered heterocycle. In some embodiments, R is phenyl, $R^1$ is methyl, X is bromine, and $R^5$ and $R^6$ together form a five membered heterocycle. In some embodiments, R is phenyl, $R^1$ is hydrogen, X is chlorine, and $R^5$ and $R^6$ together form a five membered heterocycle. In some embodiments, R is phenyl, $R^1$ is methyl, X is chlorine, and $R^5$ and $R^6$ together form a five membered heterocycle.

The compound of formula 4 or Formula 5, 6, 7 or 8, is an intermediate compound which may be used in the method of synthesis of the compound of the invention, and the invention therefore provides for the compound of formula 4, 5, 6, 7 or 8, and its use in the synthesis of nucleoside monomers, such as acyl protected L-XNA-G, such as acyl protected L-LNA-G monomers.

The intermediate compound for formula 4 (such as compounds of formula 5, 6, 7, and 8) may be made is a prestep (Step A) by reacting the compound of formula 9 or formula 9a, with phosphorus trihalide, such as $PCl_3$, $PBr_3$ or $PI_3$, such as $PCl_3$, Formula 9

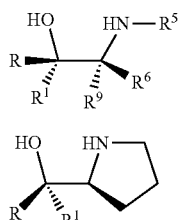

Formula 9a

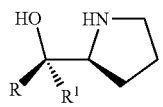

wherein R, $R^1$, $R^5$, $R^9$ and $R^6$ are as according to the compound of the invention.

The reaction between the compound of formula 9 or 9a and the phosphorus trihalide is typically performed in the presence of a tertiary non nucleophilic base, such as N-methylmorpholine (NMM), triethylamine, pyridine, N-Methylimidazole, or 1,4-Diazabicyclo[2.2.2]octane and may be performed in a solvent, such as toluene, THF, dioxane, diethylether or benzene, such as THF or toluene. In some embodiments, the tertiary non nucleophilic amine is NMM and the solvent is either toluene or THF.

In some embodiments of formula 9 or 9a, R is phenyl and $R^1$ is hydrogen. In some embodiments R is phenyl and $R^1$ is methyl.

The invention provides for a method for the synthesis of the compound of formula 4, 5, 6, 7, or 8 (which may be referred to in some embodiments described herein as step A) Said method comprising the step of reacting a compound for formula 9 or 9a with a solvent (e.g. toluene) solution of phosphorous trihalide (to make the compound of formula 4 and 5*), such as phosphorus trichloride (to make the compound of formula 6*), phosphorous triiodide (to make the compound of formula 7*), or phosphorus tribromide (to make the compound of formula 8*), at a temperature below 0° C., to produce the compound of formula 4, 5, 6, 7, 8 or 9. The solvent, may for example be selected from the group consisting of toluene, THF, dioxane, diethylether or benzene, such as THF or toluene. It will be recognised that precursor 9a may be used to make intermediates of formula 5, 6, 7, 8 or 9, depending upon which phosphorous trihalide is used (as indicated by the * in relation to formula 5, 6, 7, and 8). Therefore, the reaction of the phosphorus trihalide and the compound of formula 9 or 9a forms the intermediate compound of formula 4, 5, 6, 7 or 8.

In some embodiments the reaction of compound 9 (or 9a) and the phosphorous trihalide is performed at a temperature of about minus 45° C.-about minus 65° C., such as between about 50° C.-about minus 60° C., such as about minus 55° C. The term about includes the specific integer value indicated.

In some embodiments, phosphorus trihalide, such as $PCl_3$, is used at a molar concentration no greater than that of the compound for formula 9 or 9a. In some embodiments, a molar excess of the compound of formula 9 or 9a is used in step A, as compared to the molar quantity of phosphorous trihalide. In some embodiments the molar ratio of precursor compound of formula 9 or 9a to phosphorus trihalide in step 1 is, greater than about 1, such as 1.05 of above. In some embodiments the molar ratio of precursor compound of formula 9 or 9a to phosphorus trihalide in step 1 is no greater than 1.5.

Subsequent to synthesis, the compound for formula 4, 5, 6, 7 or 8 may be dried, such as in a vacuum, and optionally redisolved in solvent such as, such as toluene, THF, dioxane, diethylether or benzene, such as THF or toluene. for use in the subsequent synthesis step, which may be referred to herein as step B.

The invention provides for a method for the synthesis of the compound of formula 3 (which may be referred to in some embodiments described herein as step B) Said method comprising the step of reacting a compound for formula 4,

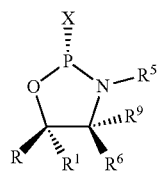

Formula 4 wherein X is halo, such as bromide, iodine or chloride (such as the compound for formula 5, 6, 7 or 8), and wherein R, $R^1$, $R^5$, $R^9$ and $R^6$ are as according to the compound of the invention, comprising the step of reacting the compound of formula 4 with a nucleoside of formula X

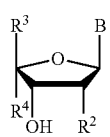

Formula X wherein, $R^2$, $R^3$ and $R^4$ are as per the compound of the invention;
in a solvent, such as, such as toluene, THF, dioxane, diethylether or benzene, such as THF or toluene; at a temperature below 0° C., to produce the compound of formula 3

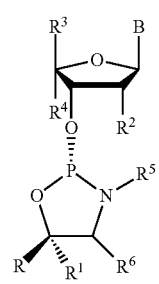

Formula 3

In some embodiments, the reaction of step is performed in the presence of an organic base, such as a tertiary non-nucleophillic amine base, such as n-methylmorpholine, and triethylamine.

In some embodiments the reaction of compound of formula 4 (or of formula 5, 6, 7 or 8) and nucleoside X is performed at a temperature of about minus 60° C.-about minus 80° C., such as between about 65° C.-about minus 75° C., such as about minus 77° C. The term about includes the specific integer value indicated.

In some embodiments the molar concentration ratio of the compound of formula 4 (or of formula 5, 6, 7 or 8) and nucleoside X used in step B is at least 2, such as about 2 and about 4, such as about 2 and about 3. In some embodiments, the compound of formula 4 (or of formula 5, 6, 7 or 8) is used in a molar excess as compared to the compound of formula X.

In some embodiments, a solution of nucleoside X is added to a solution the compound of formula 4 (or of formula 5, 6, 7 or 8) gradually, i.e. not in a single addition step, such as over a time period of at least 15 seconds, such as at least 30 seconds, such as over a period of at least 1 minute, such as at least 90 seconds, such as at least two minutes, such as between 5 and 30 minutes, such as between 10 and 20 minutes, such as about 15 minutes.

In some embodiments, the nucleoside has the formula

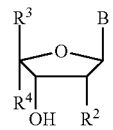

wherein, B, $R^2$, $R^3$, $R^4$, are as defined herein.

In some embodiments, the reaction in step B occurs in the presence of a base and a solvent. In some embodiments, the base is an organic base, such as a base selected from the group consisting of trimethylamine, triethylamine, and N-methylmorpholine. In some embodiments the solvent is or comprises toluene or tetrahydrofuran, optionally further comprising pyridine. In some embodiments, the solvent is or comprises a polar aprotic solvent. In some embodiments, the solvent is or comprises a solvent selected from the group consisting of acetonitrile, DMF, DMSO, dioxane, tetrahydrofuran, N-methyl-2-pyrrolidone, dichloromethane, and dichloroethane. In some embodiments, the solvent is or comprises tetrahydrofuran (THF) and the base is trimethylamine. In some embodiments, the reaction in step B occurs at a temperature below 0° C., such as below −10° C., such as below −20° C., such as below −30° C., such as below −40° C., such as below −50° C., such as below −60° C., such as below −70° C., such as between −75 and −80, such as about −77° C. About includes the exact integer mentioned.
In some embodiments the compound of formula X is selected from the compounds of formula 62, 63, 64, 65, 66, 67, 68, 69, 70 and 71:
Formula 62
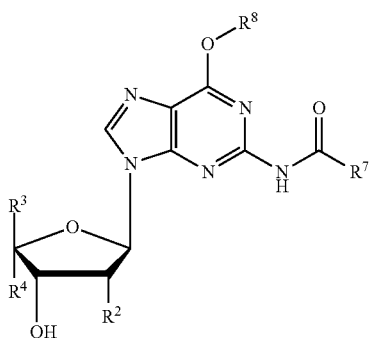
Formula 63
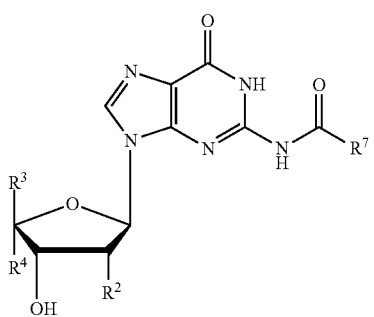
Formula 64
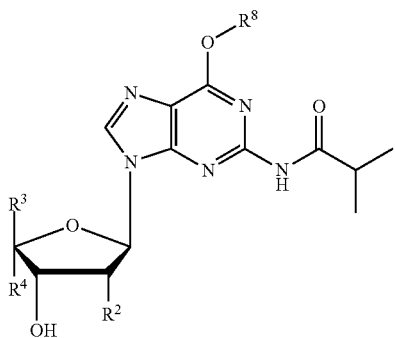
Formula 65
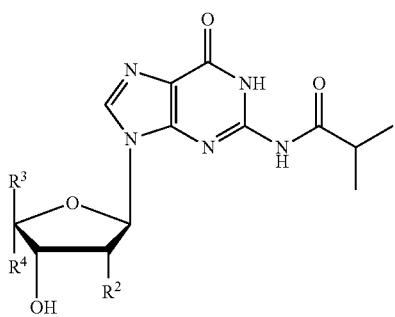
Formula 66
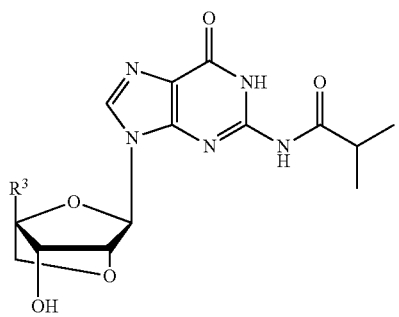
Formula 67
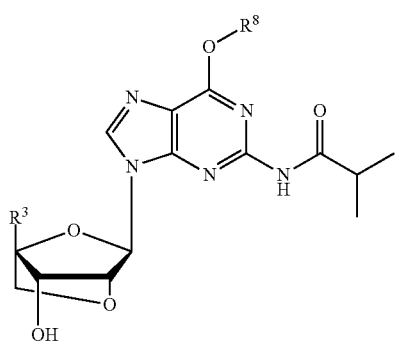
Formula 68
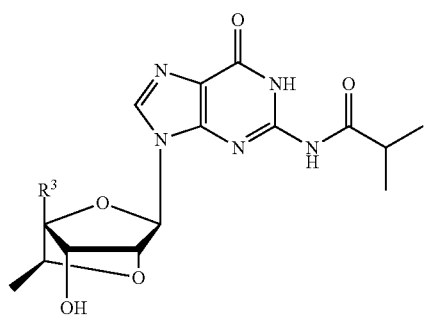
Formula 69
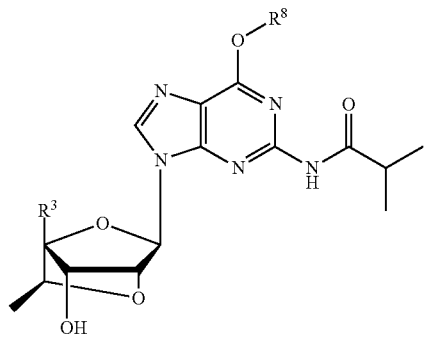

-continued

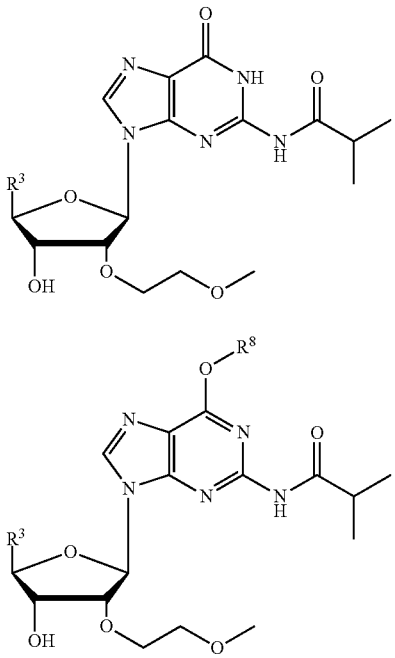

Formula 70

Formula 71

Where in $R^2$, $R^3$, $R^4$, $R^7$ and $R^8$ are as per the compound of the invention.

In some embodiments, the compound of formula X may be a compound of formula 72, 73 or 74:

Formula 72

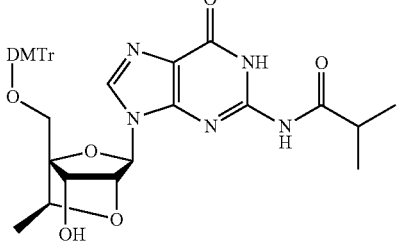

N-(9-((1R,3R,4R,6S,7S)-1-((bis(4-methoxyphenyl)(phenyl)methoxy)methyl)-7-hydroxy-6-methyl-2,5-dioxabicyclo[2.2.1]heptan-3-yl)-6-oxo-6,9-dihydro-1H-purin-2-yl)isobutyramide Formula 73

N-(9-((1R,3R,4R,7S)-1-((bis(4-methoxyphenyl)(phenyl)methoxy)methyl)-7-hydroxy-2,5-dioxabicyclo[2.2.1]heptan-3-yl)-6-oxo-6,9-dihydro-1H-purin-2-yl)isobutyramide Formula 74

N-(9-((2R,3R,4R,5R)-5-((bis(4-methoxyphenyl)(phenyl)methoxy)methyl)-4-hydroxy-3-(2-methoxyethoxy)tetrahydrofuran-2-yl)-6-oxo-6,9-dihydro-1H-purin-2-yl)isobutyramide The invention provides a method for the synthesis of a compound of formula 1 (e.g. a compound of formula 3), comprising the subsequent steps A and B. An example of the methods step A and Step B are shown in the following reaction diagram, wherein R and $R^1$ are as per the compound of the invention, $PX_3$ is phosphorus halide, X is halide, such as iodide, bromide of chloride, and B is the acyl protected guanine nucleobase of the invention.

Oligonucleotide Synthesis

The invention provides for the use of the compound according to the invention, or the solvent composition comprising the compound of the invention, in the synthesis of an oligonucleotide.

The nucleoside monomer of the invention, when incorporated into in oligonucleotide via oligonucleotide synthesis, results in the creation of a Sp stereodefined phosphorothioate internucleoside linkage, 3' to the incorporated nucleoside.

In some embodiments the oligonucleotide is a LNA oligonucleotide. The L-LNA-G monomer of the invention may be incorporated into the oligonucleotide via any suitable oligonucleotide synthesis method, such as phosphoramidite oligonucleotide synthesis. The L-LNA-G monomer of the invention is a phosphoramidite, In some embodiments the L-LNA-G monomer is incorporated into the oligonucleotide during phosphoramidite oligonucleotide synthesis.

In some embodiments, the LNA oligonucleotide made by the method of the invention may comprises at least 1 G monomers, such as at least 2 G monomers, such as at least 3 G monomers, such as at least 4 G monomers. Numerous designs of oligonucleotide are known, and the method of the invention may be used, for example to make LNA gapmers, mixmers, totalmers, and TINY LNAs.

The following figure shows a schematic representation of the reiterative cycles of oxidation, capping and de-protection which may be used in methods of phosphoramidite oligonucleotide synthesis, as exemplified below:

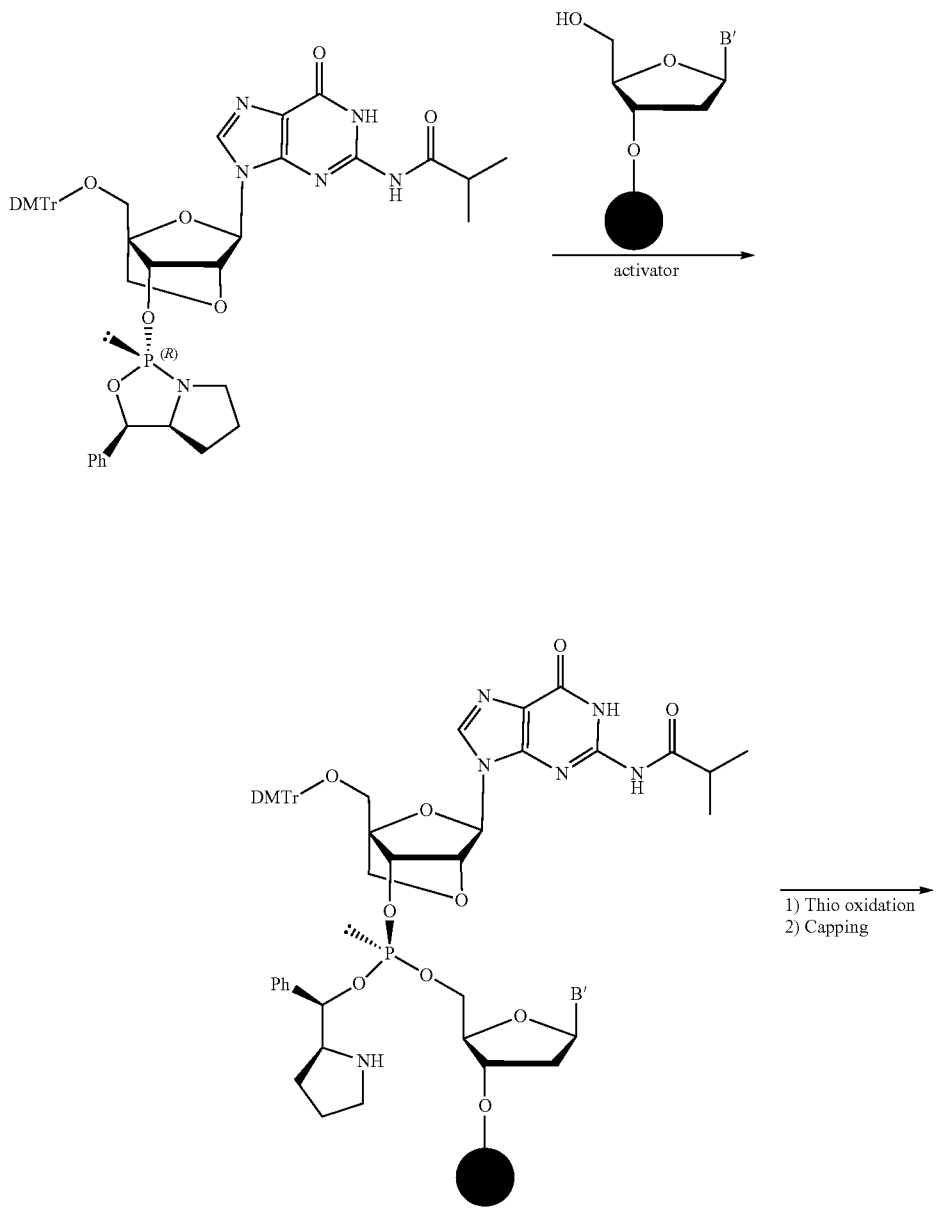

41              42
-continued
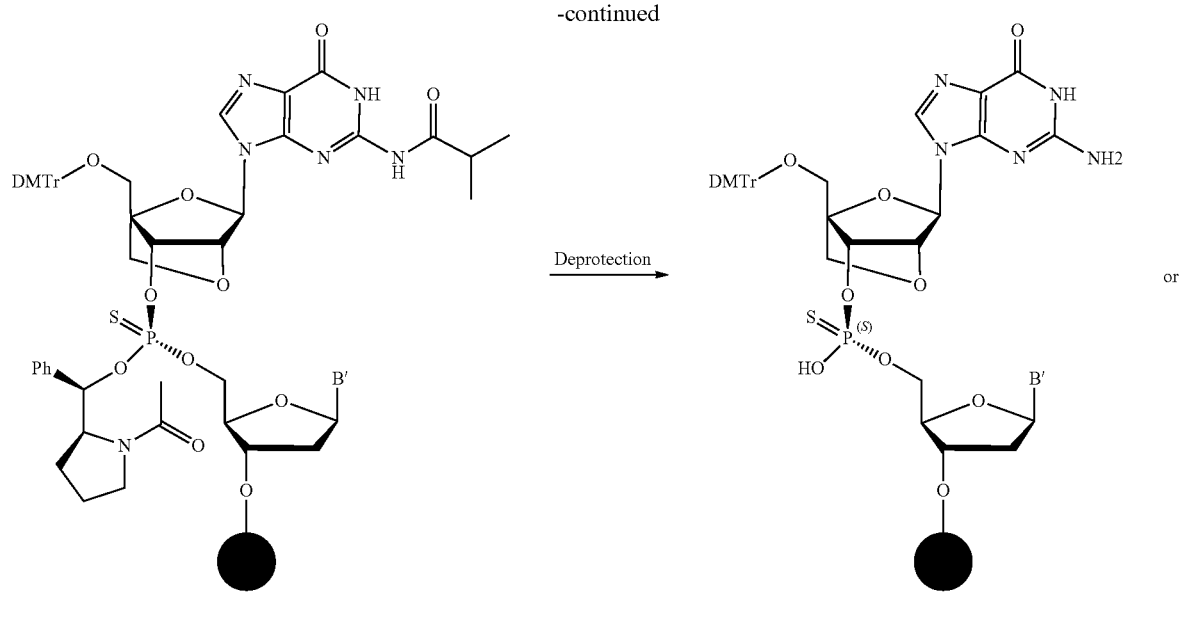
Deprotection
or
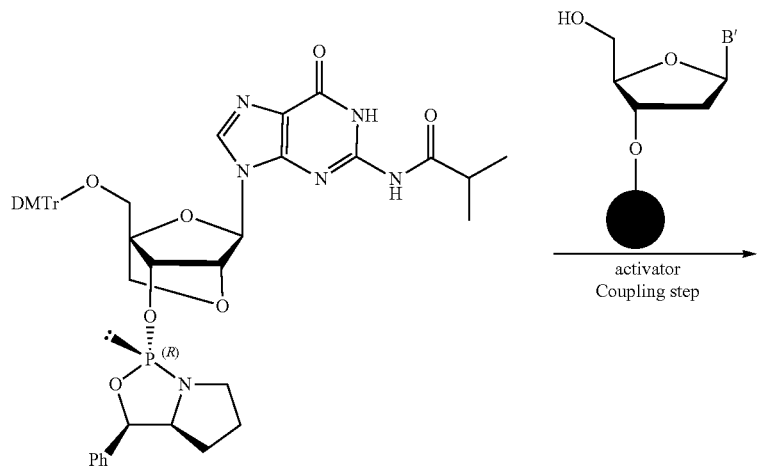
activator
Coupling step
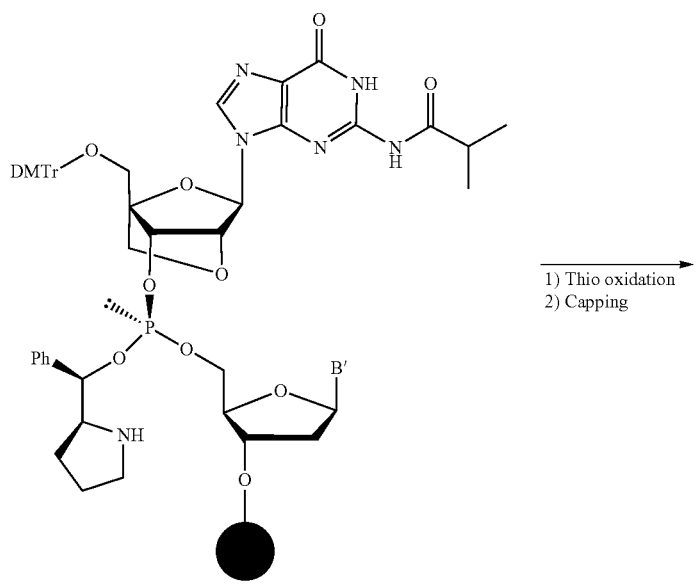
1) Thio oxidation
2) Capping -continued
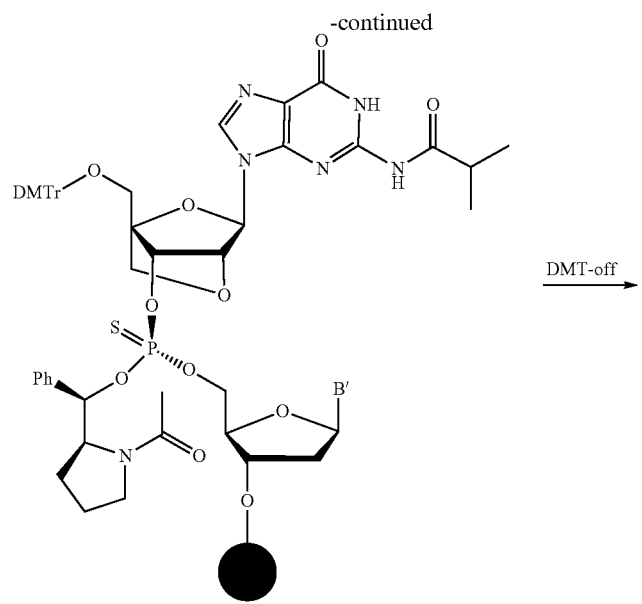
DMT-off
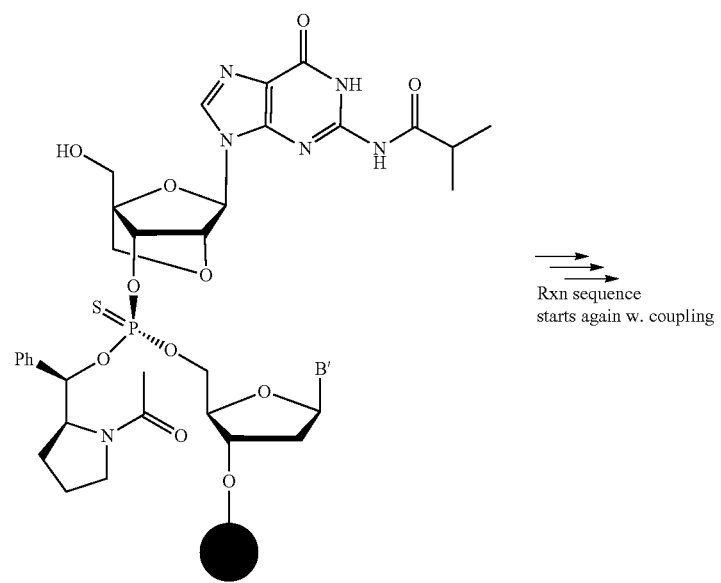
Rxn sequence
starts again w. coupling -continued

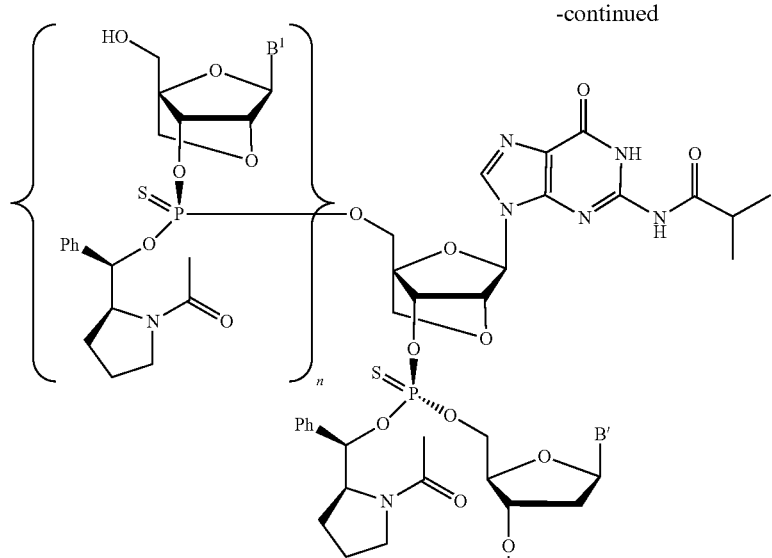

Then, continue the rxn sequence or terminate with a global deprotection →

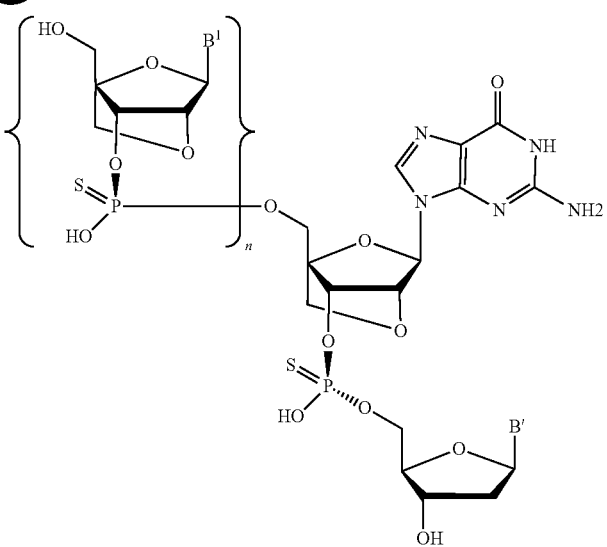

The method of preparing an oligonucleotide may utilise any suitable oligonucleotide synthesis method, such as phosphoramidite oligonucleotide synthesis.

Oligonucleotide synthesis may be performed on s solid support, such as a unylinker support. Oligonucleotide synthesis may be performed by the sequential steps of coupling, oxidation, capping and deprotection. Once the oligonucleotide has been synthesised it, any remaining protection (e.g. —C(=O)—R$^7$ and when present R$^8$) groups may be removed, and the oligonucleotide may be liberated from the solid support, for example using NH$_4$OH at 60° C.

Stereodefined Phosphorothioate Oligonucleotides

Typically, oligonucleotide phosphorothioates are synthesised as a random mixture of Rp and Sp phosphorothioate linkages (also referred to as a diastereomeric mixture). In the method of the present invention, phosphorothioate oligonucleotides are provided where at least one of the phosphorothioate linkages of the oligonucleotide is stereodefined, i.e. is either Rp or Sp in at least 75%, such as at least 80%, or at least 85%, or at least 90% or at least 95%, or at least 97%, such as at least 98%, such as at least 99%, or (essentially) all of the oligonucleotide molecules present in the oligonucleotide sample. Stereodefined oligonucleotides comprise at least one phosphorothioate linkage which is stereodefined. The term stereodefined, may be used to describe a defined chirality of one or more phosphorothioate internucleoside linkages as either Rp or Sp, or may be used to described a oligonucleotide which comprises such a (or more) phosphorothioate internucleoside linkage. It is recognised that a stereodefined oligonucleotide may comprise a small amount of the alternative stereoisomer at any one position, for example Wan et al reports a 98% stereoselectivity for the gapmers reported in NAR, November 2014.

LNA Oligonucleotide

An LNA oligonucleotide is an oligonucleotide which comprises at least one LNA nucleoside. The LNA oligonucleotide may be an antisense oligonucleotide. The term oligonucleotide as used herein is defined as it is generally understood by the skilled person as a molecule comprising two or more covalently linked nucleosides. For use as an antisense oligonucleotide, oligonucleotides are typically synthesised as 7-30 nucleotides in length.

The term "antisense oligonucleotide" as used herein is refers to oligonucleotides capable of modulating expression of a target gene by hybridizing to a target nucleic acid, in particular to a contiguous sequence on a target nucleic acid. An antisense oligonucleotide can also be defined by it's complementary to a target nucleic acid. Antisense oligonucleotides are single stranded. Antisense oligonucleotides are not essentially double stranded and are not therefore siRNAs. An antisense oligonucleotide comprises a contiguous nucleotide which is complementary to a target nucleic acid. Antisense oligonucleotides typically comprise one or more modified internucleoside linkages, and may by way of a non-limiting example be in the form of a a LNA gapmer or a mixed wing gapmer. In other embodiments the oligonucleotide may be an LNA mixmers (LNA and non-LNA nucleotides, e.g. LNA and DNA (see e.g. WO2007/112754 hereby incorporated by reference), or LNA and 2'-O-MOE nucleotides, or LNA, DNA and 2'O-MOE nucleotides), or a LNA totalmers (only LNA nucleotides—see. E.g. WO2009/043353 hereby incorporated by reference).

The term "modified internucleoside linkage" is defined as generally understood by the skilled person as linkages other than phosphodiester (PO) linkages, that covalently couples two nucleosides together. Modified internucleoside linkages are particularly useful in stabilizing oligonucleotides for in vivo use, and may serve to protect against nuclease cleavage. A phosphorothioate internucleoside linkage is particularly useful due to nuclease resistance, beneficial pharmakokinetics and ease of manufacture. In some embodiments at least 70%, such as at least 80 or such as at least 90% of the internucleoside linkages in the oligonucleotide, or contiguous nucleotide sequence thereof, are phosphorothioate. In some embodiments all of the internucleoside linkages of the oligonucleotide, or contiguous nucleotide sequence thereof, are phosphorothioate, wherein at least one of the phosphorothioate internucleoside linkages is a stereodefined phosphorothioate internucleoside linkage (originating from the incorporation of the acyl protected L-XNA-G monomer of the invention into the oligonucleotide during oligonucleotide synthesis). Further internucleoside linkers are disclosed in WO2009/124238 (incorporated herein by reference).

The term nucleobase includes the purine (e.g. adenine and guanine) and pyrimidine (e.g. uracil, thymine and cytosine) moiety present in nucleosides and nucleotides which form hydrogen bonds in nucleic acid hybridization. In the context of the present invention the term nucleobase also encompasses modified nucleobases which may differ from naturally occurring nucleobases, but are functional during nucleic acid hybridization. In some embodiments the nucleobase moiety is modified by modifying or replacing the nucleobase. In this context "nucleobase" refers to both naturally occurring nucleobases such as adenine, guanine, cytosine, thymidine, uracil, xanthine and hypoxanthine, as well as non-naturally occurring variants. Such variants are for example described in Hirao et al (2012) Accounts of Chemical Research vol 45 page 2055 and Bergstrom (2009) Current Protocols in Nucleic Acid Chemistry Suppl. 37 1.4.1.

Nucleotides are the building blocks of oligonucleotides and polynucleotides, and for the purposes of the present invention include both naturally occurring and non-naturally occurring nucleotides. In nature, nucleotides, such as DNA and RNA nucleotides comprise a ribose sugar moiety, a nucleobase moiety and one or more phosphate groups (which is absent in nucleosides). Modified nucleosides and nucleotides are modified as compared to the equivalent DNA or RNA nucleoside/tide by the introduction of a modification to the ribose sugar moiety, the nucleobase moiety, or in the case of modified nucleotides, the internucleoside linkage. Nucleosides and nucleotides may also interchangeably be referred to as "units" or "monomers".

The term "modified nucleoside" or "nucleoside modification" as used herein refers to nucleosides modified as compared to the equivalent DNA or RNA nucleoside by the introduction of one or more modifications of the sugar moiety or the (nucleo)base moiety. The term modified nucleoside may also be used herein interchangeably with the term "nucleoside analogue" or modified "units" or modified "monomers". Examples of modified nucleosides are described in the separate section "Oligomer modifications" and its sub-sections.

Acyl Protected Exocyclic Nitrogen

The exocyclic nitrogen group of guanine is illustrated below (encircled). This group is protected by an acyl group in the compound of the invention. The oxygen group may optionally also be protected.

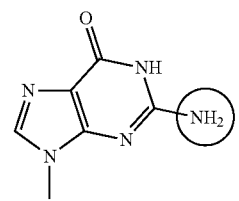

L-XNA-G Monomers

In some embodiments, the compound of the invention comprises a nucleoside moiety (Z) which is other than DNA or RNA, such monomers are referred to as L-XNA-G monomers. The "L" annotation in L-XNA-G (and L-LNA-G) refers to the stereochemistry at the stereocenter R/R$^1$ (and the stereocenter at the R$^9$ position, such as R$^6$/R$^9$ position) as shown in formula 1, 2 and 3. The alternative stereoisomer, the D-form has the reverse stereochemistry at the R/R$^1$ and R$^9$ stereocenters.

Nucleosides other than DNA and RNA may be referred to as nucleoside analogues. The nucleosides may be high affinity nucleosides (high affinity nucleoside analogues). Such monomers include, but are not limited to LNA monomers (L-LNA-G monomers), as well as 2' substituted nucleosides, such as 2'O-MOE, 2'-fluoro or 2'OMethyl. Other 2' substitutions are known in the art and some are listed under the definition of R$^2$ herein.

The LNA G Monomer

The term LNA-G refers to a nucleoside which comprises a 2'-4' biradical in the furanse ring and a guanine nucleobase. The invention provides L-LNA-G monomers, where the non cyclic nitrogen group is protected by use of an acyl protection group. Optionally the oxygen atom of the G residue is also protected.

Locked Nucleic Acid Nucleosides (LNA).

LNA nucleosides are modified nucleosides which comprise a linker group (referred to as a biradicle or a bridge) between C2' and C4' of the ribose sugar ring of a nucleotide (i.e. the embodiment where R$^2$ and R$^4$ together designate a bivalent bridge).

These nucleosides are also termed bridged nucleic acid or bicyclic nucleic acid (BNA) in the literature.

In some embodiments, the monomer of the invention is or comprises a LNA nucleoside, e.g. the compound of the invention may be of formula I or II:

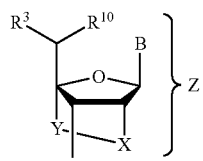

Formula I

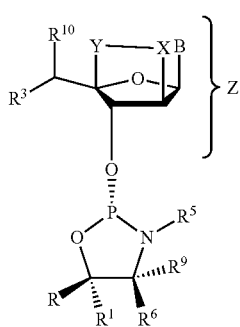

Formula II

The annotation Z represents the acyl protected guanine nucleoside (Z) of the compound of the invention—it is included for illustrative purposes.

B designates the acyl protected guanine nucleobase; R, $R^1$, $R^6$, $R^3$, $R^9$, $R^5$ are as according to the compound of the invention.

X designates a group selected from the list consisting of —C($R^a R^b$)—, —C($R^a$)=C($R^b$)—, —C($R^a$)=N—, —O—, —Si($R^a$)$_2$—, —S—, —SO$_2$—, —N($R^a$)—, and >C=Z In some embodiments, X is selected from the group consisting of: —O—, —S—, NH—, N$R^a R^b$, —CH$_2$—, CR$^a R^b$, —C(=CH$_2$)—, and —C(=CR$^a R^b$)—

In some embodiments, X is —O—

Y designates a group selected from the group consisting of —C($R^a R^b$)—, —C($R^a$)=C($R^b$)—, —C($R^a$)=N—, —O—, —Si($R^a$)$_2$—, —S—, —SO$_2$—, —N($R^a$)—, and >C=Z In some embodiments, Y is selected from the group consisting of: —CH$_2$—, —C($R^a R^b$)—, —CH$_2$CH$_2$—, —C($R^a R^b$)—C($R^a R^b$)—, —CH$_2$CH$_2$CH$_2$—, —C($R^a R^b$)C($R^a R^b$)C($R^a R^b$)—, —C($R^a$)=C($R^b$)—, and —C($R^a$)=N—

In some embodiments, Y is selected from the group consisting of: —CH$_2$—, —CHR$^a$—, —CHCH$_3$—, CR$^a R^b$— or —X—Y— together designate a bivalent linker group (also referred to as a radicle) together designate a bivalent linker group consisting of 1, 2, or 3 groups/atoms selected from the group consisting of —C($R^a R^b$)—, —C($R^a$)=C($R^b$)—, —C($R^a$)=N—, —O—, —Si($R^1$)$_2$—, —S—, —SO$_2$—, —N($R^a$)—, and >C=Z, In some embodiments, —X—Y— designates a biradicle selected from the groups consisting of: —X—CH$_2$—, —X—CR$^a R^b$—, —X—CHR$^a$—, —X—C(HCH$_3$)—, —O—Y—, —O—CH$_2$—, —S—CH$_2$—, —NH—CH$_2$—, —O—CHCH$_3$—, —CH$_2$—O—CH$_2$—, —O—CH(CH$_3$CH$_3$)—, —O—CH$_2$—CH$_2$—, OCH$_2$—CH$_2$—CH$_2$—, —O—CH$_2$OCH$_2$—, —O—NCH$_2$—, —C(=CH$_2$)—CH$_2$—, —NR$^a$—CH$_2$—, N—O—CH$_2$, —S—CR$^a R^b$— and —S—CHR$^a$—.

In some embodiments —X—Y— designates —O—CH$_2$— or —O—CH(CH$_3$)—.

and $R^a$ and, when present $R^b$, each is independently selected from hydrogen, optionally substituted C$_{1-6}$-alkyl, optionally substituted C$_{2-6}$-alkenyl, optionally substituted C$_{2-6}$-alkynyl, hydroxy, optionally substituted C$_{1-6}$-alkoxy, C$_{2-6}$-alkoxyalkyl, C$_{2-6}$-alkenyloxy, carboxy, C$_{1-6}$-alkoxycarbonyl, C$_{1-6}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di(C$_{1-6}$-alkyl)amino, carbamoyl, mono- and di(C$_{1-6}$-alkyl)-aminocarbonyl, amino-C$_{1-6}$-alkyl-aminocarbonyl, mono- and di(C$_{1-6}$-alkyl)amino-C$_{1-6}$-alkyl-aminocarbonyl, C$_{1-6}$-alkyl-carbonylamino, carbamido, C$_{1-6}$-alkanoyloxy, sulphono, C$_{1-6}$-alkylsulphonyloxy, nitro, azido, sulphanyl, C$_{1-6}$-alkylthio, halogen, where aryl and heteroaryl may be optionally substituted and where two geminal substituents $R^a$ and $R^b$ together may designate optionally substituted methylene (=CH$_2$), wherein for all chiral centers, asymmetric groups may be found in either R or S orientation.

$R^{10}$ may be hydrogen or in some embodiments may be selected from the group consisting of: optionally substituted C$_{1-6}$-alkyl, optionally substituted C$_{2-6}$-alkenyl, optionally substituted C$_{2-6}$-alkynyl, hydroxy, C$_{1-6}$-alkoxy, C$_{2-6}$-alkoxyalkyl, C$_{2-6}$-alkenyloxy, carboxy, C$_{1-6}$-alkoxycarbonyl, C$_{1-6}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di(C$_{1-6}$-alkyl)amino, carbamoyl, mono- and di(C$_{1-6}$-alkyl)-aminocarbonyl, amino-C$_{1-6}$-alkyl-aminocarbonyl, mono- and di(C$_{1-6}$-alkyl)amino-C$_{1-6}$-alkyl-aminocarbonyl, C$_{1-6}$-alkyl-carbonylamino, carbamido, C$_{1-6}$-alkanoyloxy, sulphono, C$_{1-6}$-alkylsulphonyloxy, nitro, azido, sulphanyl, C$_{1-6}$-alkylthio, halogen, where aryl and heteroaryl may be optionally substituted, and where two geminal substituents together may designate oxo, thioxo, imino, or optionally substituted methylene.

In some embodiments $R^{10}$ is selected from C$_{1-6}$ alkyl, such as methyl, and hydrogen.

In some embodiments $R^{10}$ is hydrogen.

In some embodiments, $R^a$ is either hydrogen or methyl. In some embodiments, when present, $R^b$ is either hydrogen or methyl.

In some embodiments, one or both of $R^a$ and $R^b$ is hydrogen

In some embodiments, one of $R^a$ and $R^b$ is hydrogen and the other is other than hydrogen In some embodiments, one of $R^a$ and $R^b$ is methyl and the other is hydrogen In some embodiments, both of $R^a$ and $R^b$ are methyl.

In some embodiments, the biradicle —X—Y— is —O—CH$_2$—, and $R^{10}$ is hydrogen. In some embodiments, the biradicle —X—Y— is —S—CH$_2$—, and $R^{10}$ is hydrogen.

In some embodiments, the biradicle —X—Y— is —NH—CH$_2$—, and $R^{10}$ is hydrogen.

In some embodiments, the biradicle —X—Y— is —O—CH$_2$—CH$_2$— or —O—CH$_2$—CH$_2$—CH$_2$—, and $R^{10}$ is hydrogen.

In some embodiments, the biradicle —X—Y— is —O—CH$_2$—, and R$^{10}$ is C$_{1-6}$ alkyl, such as methyl.

In some embodiments, the biradicle —X—Y— is —O—CR$^a$R$^b$—, wherein one or both of R$^a$ and R$^b$ are other than hydrogen, such as methyl, and R$^{10}$ is C$_{1-6}$ alkyl, such as methyl.

In some embodiments, the biradicle —X—Y— designate the bivalent linker group —O—CH(CH$_2$OCH$_3$)— (2' O-methoxyethyl bicyclic nucleic acid—Seth at al., 2010, J. Org. Chem., 2010, 75 (5), pp 1569-1581). In some embodiments, the biradicle —X—Y— designate the bivalent linker group —O—CH(CH$_2$CH$_3$)— (2'O-ethyl bicyclic nucleic acid—Seth et al., 2010, J. Org. Chem). In some embodiments, the biradicle —X—Y— is —O—CHR$^a$—, and R$^{10}$ is hydrogen.

In some embodiments, the biradicle —X—Y— is —O—CH(CH$_2$OCH$_3$)—, and R$^{10}$ is hydrogen. Such LNA nucleosides are also known as cyclic MOEs in the art (cMOE) and are disclosed in WO07090071.

In some embodiments, the biradicle —X—Y— designate the bivalent linker group —O—CH(CH$_3$)— in either the R- or S-configuration. In some embodiments, the biradicle —X—Y— together designate the bivalent linker group —O—CH$_2$—O—CH$_2$— (Seth at al., 2010, J. Org. Chem). In some embodiments, the biradicle —X—Y— is —O—CH (CH$_3$)—, and R$^{10}$ is hydrogen. Such 6' methyl LNA nucleosides are also known as cET nucleosides in the art, and may be either (S)cET or (R)cET stereoisomers, as disclosed in WO07090071 (beta-D) and WO2010/036698 (alpha-L).

In some embodiments, the biradicle —X—Y— is —O— CR$^a$R$^b$—, wherein in neither R$^a$ or R$^b$ is hydrogen, and R$^{10}$ is hydrogen. In some embodiments, R$^a$ and R$^b$ are both methyl.

In some embodiments, the biradicle —X—Y— is —S—CHR$^a$—, and R$^{10}$ is hydrogen.

In some embodiments, the biradicle —X—Y— is —C(=CH$_2$)—C(R$^a$R$^b$)—, such as —C(=CH$_2$)—CH$_2$—, or —C(=CH$_2$)—CH(CH$_3$)—, and R$^{10}$ is hydrogen.

In some embodiments the biradicle —X—Y— is —N(OR$^a$)—, and R$^{10}$ is hydrogen. In some embodiments R$^a$ is C$_{1-6}$ alkyl such as methyl. In some embodiments, the biradicle —X—Y— together designate the bivalent linker group —O—NR$^a$—CH$_3$— (Seth at al., 2010, J. Org. Chem). In some embodiments the biradicle —X—Y— is —N(R$^a$)—, and R$^{10}$ is hydrogen. In some embodiments R$^a$ is C$_{1-6}$ alkyl such as methyl.

In some embodiments, and R$^{10}$ is C$_{1-6}$ alkyl such as methyl. In such an embodiment, the biradicle —X—Y— may be selected from —O—CH$_2$— or —O—C(HCR$^a$)—, such as —O—C(HCH$_3$)—.

In some embodiments, the biradicle is —CR$^a$R$^b$—O—CR$^a$R$^b$—, such as CH$_2$—O—CH$_2$—, and R$^{10}$ is hydrogen. In some embodiments R$^a$ is C$_{1-6}$ alkyl such as methyl.

In some embodiments, the biradicle is —O—CR$^a$R$^b$—O—CR$^a$R$^b$—, such as O—CH$_2$—O—CH$_2$—, and R$^{10}$ is hydrogen. In some embodiments R$^a$ is C$_{1-6}$ alkyl such as methyl.

It will be recognized than, unless specified, the LNA nucleosides may be in the beta-D or alpha-L stereoisoform.

As illustrated in the examples, in some embodiments of the invention the LNA nucleosides are or comprise beta-D-oxy-LNA nucleosides, such as where the 2'-4' bridge is as per formula I, and where X is oxygen, Y is CH$_2$, and R$^{10}$ is hydrogen.

Gapmer

The term gapmer as used herein refers to an antisense oligonucleotide which comprises a region of RNase H recruiting oligonucleotides (gap) which is flanked 5' and 3' by one or more affinity enhancing modified nucleosides (flanks). Various gapmer designs are described herein. Headmers and tailmers are oligonucleotides capable of recruiting RNase H where one of the flanks are missing, i.e. only one of the ends of the oligonucleotide comprises affinity enhancing modified nucleosides. For headmers the 3' flank is missing (i.e. the 5' flank comprise affinity enhancing modified nucleosides) and for tailmers the 5' flank is missing (i.e. the 3' flank comprises affinity enhancing modified nucleosides).

LNA Gapmer

The term LNA gapmer is a gapmer oligonucleotide wherein at least one of the affinity enhancing modified nucleosides is an LNA nucleoside.

Mixed Wing Gapmer

The term mixed wing gapmer refers to a LNA gapmer wherein the flank regions comprise at least one LNA nucleoside and at least one non-LNA modified nucleoside, such as at least one 2' substituted modified nucleoside, such as, for example, 2'-O-alkyl-RNA, 2'-O-methyl-RNA, 2'-alkoxy-RNA, 2'-O-methoxyethyl-RNA (MOE), 2'-amino-DNA, 2'-Fluoro-DNA, arabino nucleic acid (ANA), 2'-fluoro-ANA and 2'-F-ANA nucleoside(s). In some embodiments the mixed wing gapmer has one flank which comprises LNA nucleosides (e.g. 5' or 3') and the other flank (3' or 5' respectfully) comprises 2' substituted modified nucleoside(s).

Length

When referring to the length of a nucleotide molecule as referred to herein, the length corresponds to the number of monomer units, i.e. nucleotides, irrespective as to whether those monomer units are nucleotides or nucleotide analogues. With respect to nucleotides, the terms monomer and unit are used interchangeably herein.

The process of the present invention is particularly suitable for the purification of short oligonucleotides, for example, consisting of 7 to 30 nucleotides, such as 7-10, such as 7, 8, 9, 10 or 10 to 20 nucleotides, such as 12 to 18 nucleotides, for example, 12, 13, 14, 15, 16, 17 or 18 nucleotides.

Further Embodiments of the Invention

1. A compound of formula 1

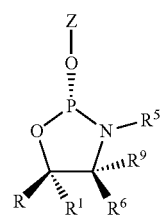

Formula 1 wherein

Z is a guanine nucleoside wherein the guanine nucleobase group comprises an acyl protection group on the guanine exocyclic nitrogen group, wherein the exocyclic oxygen of Formula I is covalently attached to the 3' carbon of the nucleoside Z;

R$^5$ and R$^6$ are independently selected from the group consisting of hydrogen, alkyl, cyclo-alkyl, aryl, heteroaryl, substituted alkyl, substituted cyclo-alkyl, substituted aryl, and substituted heteroaryl, or R$^5$ and R$^6$ together form a heterocyclic ring comprising 3-16 carbon atoms, together with the N atom of formula (I);

$R^1$ is selected from the groups consisting of hydrogen and $C_{1-3}$ alkyl; $R^9$ is hydrogen; and R is selected from the groups consisting of aryl, heteroaryl, substituted aryl, substituted heteroaryl, nitro, halogen, cyano, silyl, substituted silyl, sulfone, substituted sulfone (aryl substituted sulfone), fluorene, and substituted fluorene.

2. The compound according to embodiment 1, wherein R is selected from the group consisting of aryl, heteroaryl, substituted aryl and substituted heteroaryl.

3. The compound according to embodiment 1, wherein R is aryl, such as phenyl.

4. The compound according to any one of embodiments 1-3, wherein $R^1$ is hydrogen.

5. The compound according to any one of embodiments 1-3, wherein $R^1$ is $C_{1-3}$ alkyl, such as methyl.

6. The compound according to any one of embodiments 1-5, wherein $R^5$ and $R^6$ together form a heterocyclic ring comprising 3-16 (e.g. 4) carbon atoms, together with the N atom of formula (I)

7. The compound according to any one of embodiments 1-5, wherein $R^5$ and $R^6$ together form a heterocyclic ring comprising 4 carbon atoms, together with the N atom of formula (I).

8. The compound according to embodiment 6 or 7 wherein, the compound is of formula 2

Formula 2

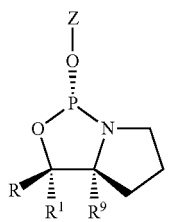

wherein Z, R, and $R^1$ are as according to any one of embodiments 1-7.

9. The compound according to any one of embodiments 1-8, wherein the compound is of formula 3

Formula 3

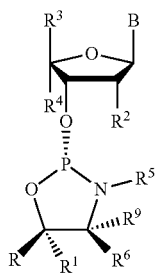

wherein,

R, $R^1$, $R^5$, $R^6$ and $R^9$ are as according to any one of embodiments 1-8;

B is the guanine nucleobase group comprising an acyl protecting group on the guanine exocyclic nitrogen group;

$R^3$=is selected from the group consisting of $CH_2ODMTr$, $CH_2$-Alkyl-O-DMTr, CH-Me-O-DMTr, $CH_2OMMTr$, $CH_2$-Alkyl-O-MMTr, CH(Me)-O-MMTr, CH—$R^a$—O-DMTrR$^b$, and CH—$R^a$—O-MMTrR$^b$;

$R^2$ is selected from the groups consisting of halo, such as —F, amino, azido, —SH, —CN, —OCN, —$CF_3$, —$OCF_3$, —O($R_m$)-alkyl, —S($R_m$)-alkyl, —N($R_m$)-alkyl, —O($R_m$)-alkenyl, —S($R_m$)-alkenyl, —N($R_m$)-alkenyl; —O($R_m$)-alkynyl, —S($R_m$)-alkynyl or —N($R_m$)-alkynyl; O-alkylenyl-O-alkyl, alkynyl, alkaryl, aralkyl, O-alkaryl, O-aralkyl, $O(CH_2)_2SCH_3$, O—$(CH_2)_2$—O—N($R_m$)($R_n$) or O—$CH_2$C(=O)—N($R_m$)($R_n$), —O—$(CH_2)_2OCH_3$, and —O—$CH_3$, where each $R_m$ and $R_n$ are independently, H, an amino protecting group or substituted or unsubstituted $C_{1-10}$ alkyl;

$R^4$=is selected from the group consisting of alkyl, cycloalkyl, cyclo-heteroalkyl, O-alkyl, S-alkyl, NH-alkyl, and hydrogen;

or $R^2$ and $R^4$ together designate a bivalent bridge consisting of 1, 2, 3 groups/atoms selected from the group consisting of —C($R^aR^b$)—, —C($R^a$)=C($R^b$), —C($R^a$)=N, O, —Si($R^a$)2-, S—, —$SO_2$—, —N($R^a$)—, and >C=Z;

wherein $R^a$ and, when present $R^b$, each is independently selected from hydrogen, optionally substituted $C_{1-6}$-alkyl, optionally substituted $C_{2-6}$-alkenyl, optionally substituted $C_{2-6}$-alkynyl, hydroxy, optionally substituted $C_{1-6}$-alkoxy, $C_{2-6}$-alkoxyalkyl, $C_{2-6}$-alkenyloxy, carboxy, $C_{1-6}$-alkoxycarbonyl, $C_{1-6}$-alkylcarbonyl, formyl, aryl, aryl¬oxy-carbonyl, aryloxy, arylcarbonyl, heteroaryl, hetero¬aryloxy-carbonyl, heteroaryloxy, heteroarylcarbonyl, amino, mono- and di($C_{1-6}$-alkyl)amino, carbamoyl, mono- and di($C_{1-6}$-alkyl)-aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, where aryl and heteroaryl may be optionally substituted and where two geminal substituents Ra and Rb together may designate optionally substituted methylene (=$CH_2$), wherein for all chiral centers, asymmetric groups may be found in either R or S orientation.

10. The compound according to any one of embodiments 1-9, wherein the acyl protecting group on the guanine exocyclic nitrogen group is —C(=O)—$R^7$, wherein $R^7$ is selected from the group consisting of optionally substituted alkyl-, alkenyl-, alkynyl-, cycloalkyl- or aryl-group, preferably from an optionally substituted $C_{1-6}$-alkyl-, $C_{2-6}$-alkenyl-, $C_{2-6}$-alkinyl-, $C_{3-7}$-cycloalkyl- or phenyl-group; wherein when substituted, the substituent group may be mono or poly substituted, e.g. with one or more substituents selected from the group consisting of halogen, $C_{1-6}$-alkyl, $C_{2-6}$-alkenyl, $C_{2-6}$-alkynyl, $C_{1-6}$-alkoxy, optionally substituted aryloxy or optionally substituted aryl.

11. The compound according to any one of embodiments 1-9 wherein the acyl protecting group on the guanine exocyclic nitrogen group is selected from the group consisting of isobuturyl (iBu), Acetyl (Ac), Phenoxyacetyl (PAC), p-Isopropylphenoxyacetyl (iPrPAC), phenylacetyl, Isopropyloxyacetyl, methoxyacetyl, benzoyl, p-methoxyphenylacetyl, diphenylacetyl, cyclohexylcarbonyl, 1,1-dimethylpropanoyl, and p-tert-Butyl-phenoxyacetyl.

12. The compound according to any one of embodiments 1-9 wherein the acyl protecting group on the guanine exocyclic nitrogen group is selected from the group consisting of isobuturyl (iBu), Acetyl (Ac), phenoxyacetyl (PAC), and p-Isopropylphenoxyacetyl (iPrPAC).

13. The compound according to any one of embodiments 1-9, wherein the acyl protecting group on the guanine exocyclic nitrogen group is isobuturyl (iBu).

14. The compound according to any one of embodiments 9-13, of formula III, wherein $R^2$ and $R^4$ together designate a bivalent bridge selected from the group consisting of bridge —C($R_aR_b$)—O—, —C($R_aR_b$)C($R_aR_b$)—O—, —CH$_2$—O—, —CH$_2$CH$_2$—O—, and —CH(CH$_3$)—O—.

15. The compound according to any one of embodiments 9-13, wherein $R^2$ and $R^4$ designate the bivalent bridge —CH$_2$—O— (methylene-oxy) or —CH(CH$_3$)—O— (methyl-methylene-oxy).

16. The compound according to any one of embodiments 1-15, wherein $R^3$ is CH$_2$—O-DMTr or CH$_2$—O-MMTr.

17. The compound according to any one of embodiments 1-16, wherein the compound is of formula 16 or 17:

Formula 16

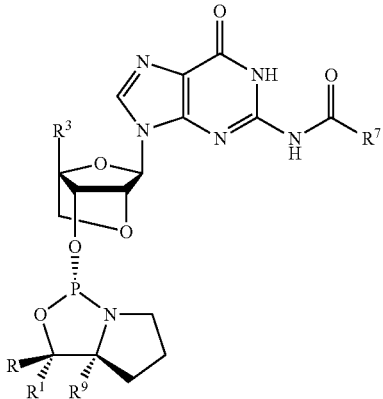

Formula 17

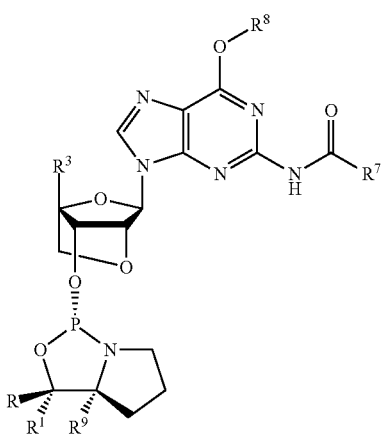

wherein R, $R^1$, $R^9$, $R^3$, $R^7$ and $R^8$ are as according to any one of embodiments 1-16.

18. The compound according to embodiment 17, wherein R is phenyl and $R^1$ is hydrogen or methyl.

19. The compound according to embodiment 17, wherein R is phenyl and $R^1$ is hydrogen.

20. The compound according to embodiment 17, wherein R is phenyl and $R^1$ is methyl.

21. The compound according to any one of embodiments 17-20, wherein the acyl protection group (—C(=O)—$R^7$) is isobutyryl.

22. A solution comprising the compound of anyone of embodiments 1-21 and a solvent.

23. The solution according to embodiment 22, wherein the solvent is or comprises a polar aprotic solvent.

24. The solution according to embodiment 22 or 23, wherein the solvent is selected from the group consisting of acetonitrile, DMF, DMSO, dioxane, tetrahydrofuran, N-methyl-2-pyrrolidone, dichloromethane, and dichloroethane.

25. The use of the compound according to any one of embodiments 1-21, or the solution according to embodiments 22-24 in the synthesis of an oligonucleotide.

26. A method for the synthesis of a compound according to any one of embodiments 1-21, said method comprising the step of reacting a guanine nucleoside comprising a 3'—OH group; with a compound of formula 4

Formula 4

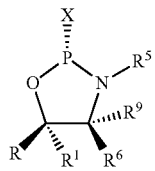

wherein X is halide, such as iodide, bromide or chloride, and wherein R, $R^1$, $R^5$, $R^9$ and $R^6$ are as according to any one of the preceding embodiments, and wherein the guanine nucleobase group on the guanine nucleoside comprises an acyl protecting group on the guanine exocyclic nitrogen group, such as the acyl protecting group of any one of embodiments 10-13.

27. The method according to embodiment 26, wherein the compound of formula 4 wherein X is chloride.

28. The method according to embodiment 26 or 27, wherein the compound of formula 4 is selected from the group consisting of

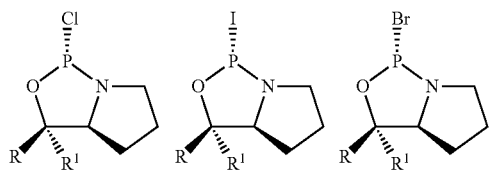

29. The method according to any one of embodiments 26-28, wherein R, $R^1$, $R^5$, $R^6$ and $R^9$ are as defined in any one of embodiments 1-25.

30. The method according to any one of embodiments 26-29, wherein the nucleoside has the formula

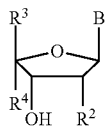

wherein, B, $R^2$, $R^3$, $R^4$, are as defined in any one of embodiments 9-25.

31. The method according to any one of embodiments 26-30, wherein the reaction step occurs in the presence of a base and a solvent.

32. The method according to embodiment 32 wherein the base is an organic base, such as a tertiary non-nucleophillic organic base, such as a base selected from the group consisting of trimethylamine, triethylamine, and N-methylmorpholine.

33. The method according to embodiment 31 or 32, wherein the solvent is selected from the group consisting of those defined in any one of embodiments 22-24.

34. The method according to any one of embodiments 26-33, wherein the solvent is or comprises tetrahydrofuran (THF) or toluene, wherein optionally the solvent my further comprise pyridine.

35. The method according to any one of embodiments 26-34, wherein the reaction occurs at a temperature below 0° C., such as below −50° C.

EXAMPLES

Example 1

General Synthesis Method

To a solution of N-methylmorpholine in toluene (50 mL) $PCl_3$ (2.93 mL 33.4 mmol) was added at −70° C. over a time course of 10 min. Hereafter, proline (P5-D or P5-L) auxilary (6.24 g 35.2 mmol) in toluene (50 mL) was added over 30 min (see *J. Am. Chem. Soc.*, 2008, 130, 16031-16037 for synthesis of P5-D and P5-L). The resulting mixture was stirred at room temperature for 1.5 h after which solvent and volatiles were removed in vacuo (40° C. and 15 mbar). Then, the remaining residue was dissolved in THF (50 mL) and hereafter cooled to −70° C. followed by the addition of first NEt3 (17.8 mL 128 mmol) and then, over 30 min, 5'-ODMT-DNA-Nucleoside (16 mmol) as a solution in THF (50 mL). The reaction mixture was stirred at −77° C. for 30 min and then for 2 h at room temperature. Hereafter, cold EtOAc (200 mL) was added and mixture was washed with cold NaHCO3 (150 mL), brine (150 mL), dried (Na2SO4), filtered, and evaporated to dryness. The crude product was purified by flash column chromatography under argon with 7% NEt3 included in the eluent to avoid degradation on silicia.

The product was obtained as a solid potentially containing small amounts of residual solvents from e.g. EtOAc, THF, and NEt3.

Using the above procedure, the following monomers were synthesized:

D-DNA A: 31P NMR (160 MHz, DMSO-d6): δ 150.3
L-DNA A: 31P NMR (160 MHz, DMSO-d6): δ 148.5
D-DNA T: 31P NMR (160 MHz, DMSO-d6): δ 151.0
L-DNA T: 31P NMR (160 MHz, DMSO-d6): δ 149.1
D-DNA C: 31P NMR (160 MHz, DMSO-d6): δ 151.7
L-DNA C: 31P NMR (160 MHz, DMSO-d6): δ 149.8
D-DNA G-i-Bu: 31P NMR (160 MHz, DMSO-d6): δ 151.7
L-DNA G-DMF: 31P NMR (160 MHz, DMSO-d6): δ 150.3

Example 2

Synthesis of D-LNA-G-DMF

5'-ODMT-LNA-G (3.51 g 5.00 mmol) was co-evaporated with pyridine and then with toluene to remove any residual water or other solvents. Then the residue was dissolved in pyridine (10 mL) and THF (10 mL). This solution was added to solution of D-oxazaphospholidine (3.51 g 5.00 mmol), $PCl_3$ (0.88 mL 10.0 mmol), and NEt3 (3.50 mL 25.0 mmol) at −77° C. The resulting reaction mixture was then stirred at −77° C. for 15 min and then at 1.5 h at room temperature. Hereafter, EtOAc (150 mL) was added and mixture was washed with cold NaHCO3 (100 mL) and brine (100 mL), dried using $Na_2SO_4$, filtered, and finally evaporated together with toluene.

The resulting residue was purified by column chromatography (eluent THF in EtOAc form 10% to 30%+7% NEt3) giving D-LNA-G-DMF (3.91 g, estimated yield 84%).

$^1$H NMR (400 MHz, DMSO-d6): δ 11.42 (1H, s), 8.56 (1H, s), 7.95 (1H, s), 7.49-7.16 (14H, m), 6.90-6.83 (4H, m), 5.96 (1H, s), 5.58 (1H, d, J=6.7 Hz), 3.87 (1H, d, J=8.1 Hz), 3.72 (6H, s), 3.62-3.54 (1H, m), 3.45 (2H, s), 3.40-3.33 (1H, m), 3.08 (3H, s), 2.99 (3H, s), 2.93-2.84 (1H, m), 1.53-1.39 (2H, m), 1.06-0.97 (1H, m), 0.79-0.63 (1H, m).

$^{31}$P NMR (160 MHz, DMSO-d6): δ 151.6

LRMS (ESI) m/z [M+H]$^+$ calcd for $C_{46}H_{49}N_7O_8P$: 858.3. Found: 858.7.

Example 3

Synthesis of L-LNA-G-DMF

5'-ODMT-LNA-G (4.91 g 7.00 mmol) was co-evaporated with pyridine and then with toluene to remove any residual water or other solvents. Then the residue was dissolved in pyridine (10 mL) and THF (15 mL). This solution was added to solution of L-oxazaphospholidine (2.48 g 14.0 mmol), $PCl_3$ (1.22 mL 14.0 mmol), and NEt3 (4.90 mL 35.0 mmol) at −77° C. The resulting reaction mixture was then stirred at −77° C. for 15 min and then at 1.5 h at room temperature. Hereafter, EtOAc (150 mL) was added and mixture was washed with cold NaHCO3 (100 mL) and brine (100 mL), dried using $Na_2SO_4$, filtered, and finally evaporated together with toluene.

The resulting residue was purified by column chromatography (eluent THF in EtOAc/DCM 1:1 using a gradient from 15% to 25%+7% NEt3) giving D-LNA-G-DMF (3.41 g, estimated yield 84%). The product was purified by column chromatography as described above.

$^1$H NMR (400 MHz, DMSO-d6): δ 12.3-11.9 (1H, br s), 11.8-11.5 (1H, br s), 8.05 (1H, s), 7.45-7.40 (2H, m), 7.35-7.21 (10H, m), 7.02-6.97 (2H, m), 6.92-6.86 (4H, m), 5.94 (1H, s), 5.09 (1H, d, J=6.5 Hz), 4.88 (1H, d, J=7.5 Hz), 4.69 (1H, s), 3.89-3.81 (2H. m), 3.74 (3H, s), 3.73 (3H, s), 3.71-3.64 (1H, m), 3.48-3.38 (3H, m), 2.83-2.73 (1H, m), 2.71-2.64 (1H, m), 1.55-1.45 (2H, m), 1.14-1.05 (1H, m), 1.08 (3H, d, J=6.9 Hz), 1.05 (3H, d, J=6.9 Hz), 0.76-0.66 (1H, m).

$^{31}$P NMR (160 MHz, DMSO-d6): δ 148.7

LRMS (ESI) m/z [M+H]$^+$ calcd for $C_{47}H_{50}N_6O_9P$: 873.3. Found: 873.7.

Example 4

Synthesis of D-DNA G-DMF

To a solution of N-methylmorpholine in toluene (50 mL) was PCl3 (2.93 mL 33.4 mmol) added at −70° C. over a time course of 10 min. Hereafter P5-D (6.24 g 35.2 mmol) in toluene (50 mL) was added over 30 min. The resulting reaction mixture was stirred at room temperature for 1.5 h after which solvent and volatiles were removed in vacuo (40° C. and 15 mbar). Then, the remaining residue was dissolved in THF (50 mL) and hereafter cooled to −70° C. followed by the addition of first NEt3 (17.8 mL 128 mmol) and then, over 30 min, 5'-ODMT-DNA-G (9.99 g 16.0 mmol) as a solution in THF (50 mL). The reaction mixture was stirred at −77° C. for 30 min and then for 2 h at room temperature. Hereafter, cold EtOAc (200 mL) was added and mixture was washed with cold NaHCO3 (150 mL), brine (150 mL), dried (Na2SO4), filtered, and evaporated to dryness. The crude product was purified by flash column chromatography under argon (eluent DCM/EtOAc=2/1+7%

NEt3). D-DNA-G-DMF was isolated as a white foam (10.6 g, 72%) with traces of solvent impurities (EtOAc, toluene, and NEt3).

$^1$H NMR (400 MHz, DMSO-d$_6$): δ 11.36 (1H, s), 8.52 (1H, s), 7.96 (1H, s), 7.40-7.16 (14H, m), 6.83-6.77 (4H, m), 6.27 (1H, t, J=6.4 Hz), 5.65 (1H, d, j=6.5 Hz), 5.08-5.01 (1H, m), 4.02-3.98 (1H, m), 3.91-3.83 (1H, m), 3.71 (6H, s), 3.45-3.35 (1H, m), 3.27-3.18 (2H, m), 3.07 (3H, s), 3.00 (3H, s), 2.97-2.88 (2H, m), 2.49-2.40 (1H, m), 1.58-1.48 (1H, m), 1.47-1.38 (1H, m), 1.16-1.09 (1H, m), 0.86-0.76 (1H, m).

$^{31}$P NMR (160 MHz, DMSO-d$_6$): δ 151.7

LRMS (ESI) m/z [M+H]$^+$ calcd for C$_{45}$H$_{47}$N$_7$O$_7$P: 828.3. Found: 828.6.

Example 5

Synthesis of L-DNA G-DMF

To solution of N-metylmorpholine in toluene (25 mL) was PCl3 (1.33 mL 15.2 mmol) during 5 minutes added at −55° C. followed with the addition of P5-L (2.84 g 16.00 mmol) in toluene (25 mL) during 15 min. The resulting reaction mixture was stirred at −55-45° C. for 10 min and then at 1.5 h at room temperature. Then, the solvent and other volatiles were removed in vacuo (40° C. and 6 mbar). The remaining residue was then dissolved in THF (25 mL) and cooled to −77° C. Hereafter, NEt3 (8.92 mL 64 mmol) was added followed by a solution of 5′-ODMT-DNA-G-DMF (4.5 g, 7.2 mmol) in THF (25 mL) during 15 min. The reaction mixture was stirred at −77° C. for 15 min and then at 3 h at room temperature. Hereafter, EtOAc (150 mL) was added and the mixture was extracted with cold NaHCO3 (100 mL), brine (50 mL), dried (Na2SO4), filtered, and evaporated.

The product was isolated by flash column chromatography under argon (eluent EtOAc/DCM=1/2+7% NEt3) as a white foam (3.77 g, 63%) together with traces of EtOAc.

$^1$H NMR (400 MHz, DMSO-d$_6$): δ 11.36 (1H, s), 8.51 (1H, s), 7.96 (1H, s), 7.39-7.11 (14H, m), 6.80-6.73 (4H, m), 6.28 (1H, t, J=6.5 Hz), 5.72 (1H, d, j=6.5 Hz), 5.06-4.96 (1H, m), 4.02-3.95 (1H, m), 3.84-3.76 (1H, m), 3.70 (3H, s), 3.69 (3H, s), 3.50-3.39 (1H, m), 3.27-3.18 (2H, m), 3.08 (3H, s), 3.02 (3H, s), 2.98-2.83 (2H. m), 2.48-2.39 (1H, m), 1.58-1.40 (2H, m), 1.12-1.02 (1H, m), 0.83-0.71 (1H, m).

$^{31}$P NMR (160 MHz, DMSO-d$_6$): δ 150.3

LRMS (ESI) m/z [M+H]$^+$ calcd for C$_{45}$H$_{49}$N$_7$O$_7$P: 830.3. Found: 830.6.

Example 6

Synthesis of L-LNA-G-Ibu Monomers

Procedure for the Synthesis of 5′-OAP-LNA-G-iBu Derivatives

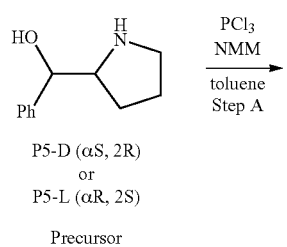

P5-D (αS, 2R)
or
P5-L (αR, 2S)

Precursor

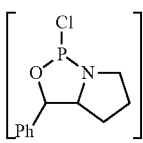

Intermediate

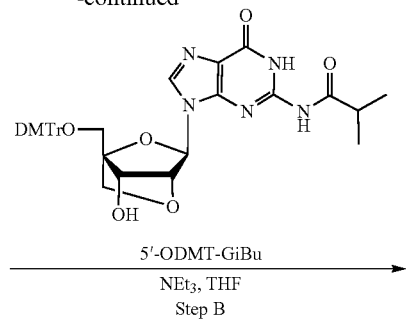

5′-ODMT-GiBu
NEt3, THF
Step B

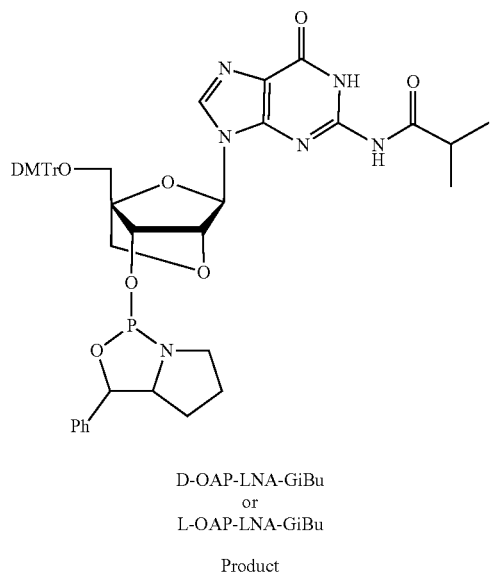

D-OAP-LNA-GiBu
or
L-OAP-LNA-GiBu

Product

Step A: To a solution of N-methylmorpholine (1.76 mL 16.0 mmol) in toluene (15 mL) was added PCl$_3$ (0.66 mL 7.6 mmol) over 5 min at −55° C. Hereafter, a solution of (S)-phenyl-(R)-pyrolidin-2yl)methanol (P5-D) (1.42 g 8.00 mmol) in toluene (12 mL) was added during the next 15 min. Then, the reaction mixture was stirred for 10 min between −55 to −45° C. and then at room temperature for 1.5 h.

Solvents and other volatile compounds were removed in vacuo at 40° C. and 6 mbar after which THF (13 mL) was added.

Step B: This was followed by a cooling of the reaction mixture to −77° C. whereafter triethylamine (5.54 mL, 40 mmol) was added followed by a solution of 5′-ODMT-LNA-G-iBu (2.67 g, 4 mmol) in THF (13 mL) over 15 min. The resulting mixture was stirred for 15 min at −77° C. and then at room temperature for 3 h. Hereafter, EtOAc (75 mL) was added and the mixture was washed with cold NaHCO$_3$ (50 mL) and brine (50 mL), dried using Na$_2$SO$_4$, filtered, and evaporated in vacuo. The crude product was purified by flash column chromatography under Ar (EtOAc:hexane, 1:4+7% NEt$_3$).

The product was obtained as a white foam (1.95 g, estimated yield of 55%).

$^{31}$P-NMR in DMSO 148.8 ppm+1% at 28.8 ppm.

Additional Optimization of the Synthesis for Both D-LNA G-iBu and L-LNA G-iBu

| No. | St. m. | molar ratio P5:PCl$_3$:5'-ODMT-LNA-G-iBu | 5'-ODMT-LNA-G-iBu, mmol | Estimated yield,[a] % |
|---|---|---|---|---|
| 1 | P5-L | 2:2:1 | 8.00 | 48 |
| 2 | P5-L | 2:1.9:1 | 4.00 | 55 |
| 3 | P5-D | 2.2:2.1:1 | 7.20 | 64 |
| 4 | P5-L | 2.4:2.4:1 | 8.00 | 64 |
| 5 | P5-L | 2.2:2.1:1 | 8.00 | 68 |

It was found that a slight excess of PCl$_3$ over the precursor (e.g. P5) causes formation of side products that significantly reduce the yield of the product (e.g. OAP-LNA-GiBu). It is therefore desirable to use at least molar equivalents of precursor & PCl$_3$. In some embodiments the molar ratio of precursor to PCl$_3$ in step 1 is, greater than about 1, such as 1.05 of above. In some embodiments the molar ratio of precursor to PCl$_3$ in step 1 is no greater than 1.5.

It was found that the use of over two fold molar equivalents of the intermediate in step 2 gave the highest yield of product (see table, entries 3 and 5). In some embodiments the molar ratio of intermediate (e.g. 5'-ODMT-G/iBu) to the precursor and PCl$_3$ is greater than 2.

The purity of the products was determined from $^{31}$P-NMR spectra.

Example 6

Determination of Stability and Solubility of Products

To investigate the stability and solubility of L-LNA G-DMF and L-LNA G-i-Bu the following experimental procedure was followed:

To a 1.5 mL vial was added 0.013 mmol of amidite after which the solid material was dissolved in 0.13 mL of solvent. Hereafter, the vial was capped, vortexed, and finally left at room temperature for 24 hours. Then, the dissolved material was visually examined regarding the solubility (FIG. 1). If the solution appeared cloudy or otherwise non-homogenous the solubility was set to "no". If the solution appeared completely homogenous the solubility was set to "yes" (examination repeated after 24 hours).

Stability Determination Method: To complete the analysis the stability of the amidite was investigated using an Agilent 1100 series HPLC-MS with from the following specifications:

Column: Waters XTerra, MS C-18, 5 µm, 2.1×100 mm
Temp: 40° C.
Flow: 0.3 mL/min
Detection: UV at 254 nm
Run time: 12 min
Eluent: A: 0.1% sat. NH4OH (aq) in H2O B: 20% A in CH$_3$CN
Time (min): % B Eluent:
0.00:80
0.50:80
3.00:100
7.00:100
8.00:80
12.00:80

The mass and UV peak of the mother compound was identified at 0 hours and at 24 hours. Hereafter, the relative stability compared to other by-products was reported by integrating the UV chromatogram (254 nm) and normalizing the area to the chromatogram recorded at 0 hours (FIG. 2).

Figure 3A:
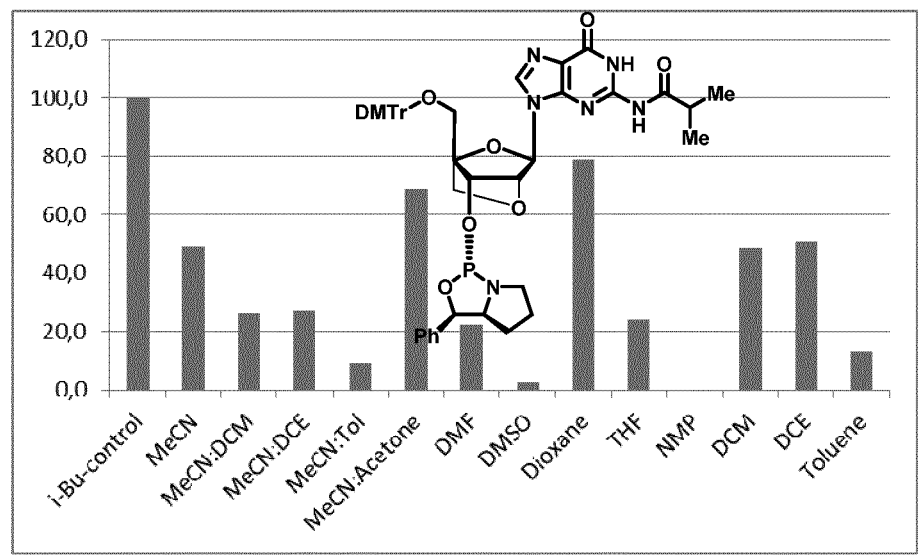
Figure 3B:
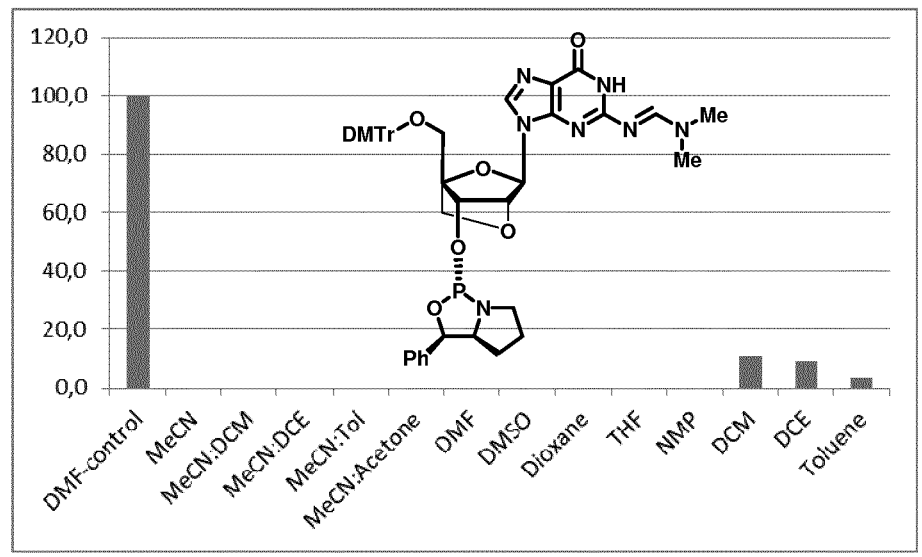

The solubility data at 0 hours and 24 hours after synthesis for the three monomers is illustrated in FIG. 1. The stability data measured after 24 hours in various solvents is shown in FIG. 2 and FIGS. 3a (L-LNA-G-iBu) and 3b (L-LNA-G-DMF).

The monomer L-LNA G-DMF is unsoluble in most solvents (MeCN, MeCN:DCE, MeCN:Tol, MeCN:acetone, Dioxane, and THF). The solvents where the monomer is souble (MeCN:DCM, DMF, DMSO, NMP, DCM, DCE, and Toluene) shows a tremoundous instability. The best solvent being DCM with 10% left of the amidite after 24 hours.

The monomer L-LNA G-i-Bu is soluble in all solvents investigated (12 different) with the best performing being MeCN, MeCN:acetone, DCM, and DCE. All solvents investigated for the L-LNA G-i-Bu monomer shows a significant improvement in solubility and stability.

TABLE 1

| Stability at 24 hours | MeCN | MeCN:DCM (1:1) | MeCN:DCE (1:1) | MeCN:Toluene (1:1) | MeCN:Acetone (1:1) | DMF | DMSO | Dioxane | THE | NMP | DCM | DCE | Toluene |
|---|---|---|---|---|---|---|---|---|---|---|---|---|---|
| D-LNA A-DMF | 2 | 3 | 3 | 3 | 2 | 3 | 3 | 2 | 1 | 3 | 1 | 1 | 3 |
| L-LNA A-DMF | 3 | 3 | 3 | 3 | 2 | 3 | 3 | 1 | 1 | 3 | 1 | 1 | 3 |
| D-LNA T-DMF | 1 | 1 | 1 | 3 | 2 | 2 | 3 | 2 | 1 | 3 | 1 | 1 | 3 |
| L-LNA T-DMF | 1 | 1 | 1 | 3 | 2 | 1 | 2 | 1 | 1 | 2 | 1 | 1 | 3 |
| D-LNA C-DMF | 3 | 3 | 3 | 3 | 3 | 3 | 3 | 2 | 2 | 3 | 1 | 1 | 3 |
| L-LNA C-DMF | 2 | 2 | 2 | 3 | 3 | 3 | 3 | 1 | 1 | 3 | 2 | 2 | 3 |
| D-LNA G-DMF | 1 | 1 | 1 | 3 | 2 | 1 | 1 | 1 | 2 | 3 | 1 | 1 | 3 |
| L-LNA G-DMF | Not soluble | 3 | Not soluble | Not soluble | Not soluble | 3 | 3 | Not soluble | Not soluble | 3 | 3 | 3 | Not soluble |
| L-LNA G-iBu | 2 | 2 | 2 | 3 | 2 | 3 | 3 | 1 | 2 | n/a | 2 | 2 | 3 |

TABLE 1-continued

| Stability at 24 hours | MeCN | MeCN:DCM (1:1) | MeCN:DCE (1:1) | MeCN:Toluene (1:1) | MeCN:Acetone (1:1) | DMF | DMSO | Dioxane | THF | NMP | DCM | DCE | Toluene |
|---|---|---|---|---|---|---|---|---|---|---|---|---|---|
| D-DNA A-DMF | 3 | 3 | 3 | 3 | 3 | 3 | 3 | 2 | 2 | 3 | 2 | 2 | 3 |
| L-DNA A-DMF | 3 | 3 | 3 | 3 | 3 | 3 | 3 | 2 | 2 | 3 | 2 | 2 | 3 |
| D-DNA T-DMF | 3 | 3 | 3 | 3 | 2 | 3 | 3 | 1 | 1 | 3 | 1 | 1 | 3 |
| L-DNA T-DMF | 3 | 3 | 3 | 3 | 3 | 3 | 3 | 1 | 2 | 3 | 1 | 1 | 3 |
| D-DNA C-DMF | 3 | 1 | 2 | 3 | 1 | 2 | 3 | 1 | 1 | 3 | 1 | 1 | 3 |
| L-DNA C-DMF | 2 | 2 | 2 | 3 | 2 | 3 | 3 | 1 | 1 | 3 | 1 | 1 | 3 |
| D-DNA G-DMF | 3 | 3 | 3 | 3 | 3 | 3 | 3 | 2 | 3 | n/a | n/a | n/a | 3 |
| L-DNA G-DMF | 2 | 3 | 3 | 3 | 3 | 3 | 3 | 2 | 3 | n/a | n/a | n/a | 3 |

TABLE 2

| | MeCN | MeCN:DCM (1:1) | MeCN:DCE (1:1) | MeCN:Tol. (1:1) | MeCN:Acetone (1:1) | DMF | DMSO | Dioxane | THF | NMP | DCM | DCE | Toluene |
|---|---|---|---|---|---|---|---|---|---|---|---|---|---|
| D-LNA G-DMF | yes | yes | yes | yes | yes | yes | yes | yes | yes | yes | yes | yes | yes |
| L-LNA G-DMF | no | yes | no | no | no | yes | yes | no | no | yes | yes | no | no |
| L-LNA Gi-Bu | yes | yes | yes | yes | yes | yes | yes | yes | yes | n/a | yes | yes | yes |

TABLE 3

| | MeCN | MeCN:DCM (1:1) | MeCN:DCE (1:1) | MeCN:Tol. (1:1) | MeCN:Acetone (1:1) | DMF | DMSO | Dioxane | THF | NMP | DCM | DCE | Toluene |
|---|---|---|---|---|---|---|---|---|---|---|---|---|---|
| D-LNA G-DMF | yes | yes | yes | yes | yes | yes | yes | yes | yes | yes | yes | yes | yes |
| L-LNA G-DMF | no | yes | yes | no | no | yes | yes | no | no | yes | yes | yes | no |
| L-LNA Gi-Bu | no | no | no | no | yes | yes | no | yes | yes | n/a | yes | yes | yes |

The invention claimed is:

1. A compound of Formula 50 or 51

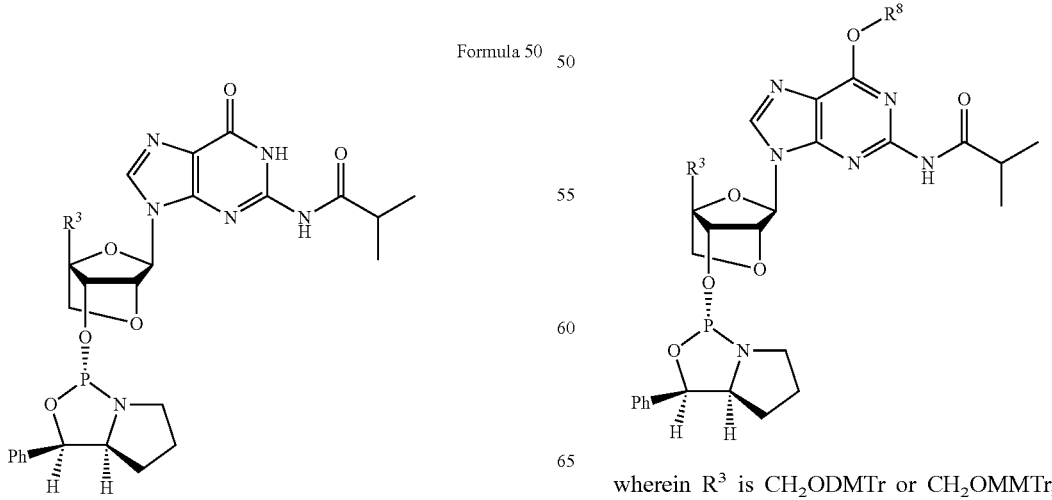

wherein $R^3$ is $CH_2ODMTr$ or $CH_2OMMTr$, and $R^8$ is cyanoethyl.

2. The compound according to Formula 51 of claim 1, wherein $R^3$ is $CH_2ODMTr$, and $R^8$ is cyanoethyl.
3. The compound according to Formula 50 of claim 1 of, wherein $R^3$ is $CH_2ODMTr$.
4. The compound according to claim 1 of Formula 76
Formula 76
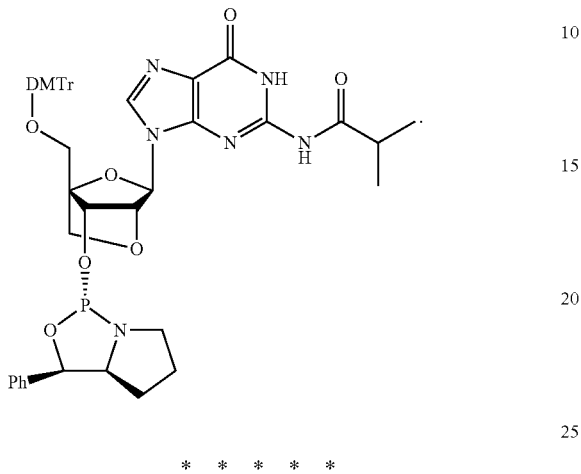
* * * * *

UNITED STATES PATENT AND TRADEMARK OFFICE
CERTIFICATE OF CORRECTION

| | |
|---|---|
| PATENT NO. | : 11,267,843 B2 |
| APPLICATION NO. | : 16/086252 |
| DATED | : March 8, 2022 |
| INVENTOR(S) | : Albaek et al. |

It is certified that error appears in the above-identified patent and that said Letters Patent is hereby corrected as shown below:

On the Title Page

Item (54) and In the Specification, Column 1, Line 1, The title should read as follows:
ACYL-PROTECTED L-LNA-GUANOSINE L-MONOMERS Signed and Sealed this
Twenty-first Day of June, 2022

Katherine Kelly Vidal
Director of the United States Patent and Trademark Office